(12) United States Patent
Shelton, IV et al.

(10) Patent No.: US 12,349,904 B2
(45) Date of Patent: Jul. 8, 2025

(54) STAPLE CARTRIDGES COMPRISING STAPLE RETENTION FEATURES

(71) Applicant: Cilag GmbH International, Zug (CH)

(72) Inventors: Frederick E. Shelton, IV, Hillsboro, OH (US); Kevin M. Fiebig, Cincinnati, OH (US); Shane R. Adams, Lebanon, OH (US); Nicholas J. Ross, Franklin, OH (US)

(73) Assignee: Cilag GmbH International, Zug (CH)

( * ) Notice: Subject to any disclaimer, the term of this patent is extended or adjusted under 35 U.S.C. 154(b) by 0 days.

(21) Appl. No.: 18/379,832

(22) Filed: Oct. 13, 2023

(65) Prior Publication Data

US 2025/0120716 A1   Apr. 17, 2025

(51) Int. Cl.
*A61B 17/072* (2006.01)

(52) U.S. Cl.
CPC .............. *A61B 17/07207* (2013.01); *A61B 2017/07271* (2013.01)

(58) Field of Classification Search
CPC ........ A61B 17/072; A61B 2017/07257; A61B 2017/07271
USPC ................ 227/175.1–182.1, 8, 19
See application file for complete search history.

(56) References Cited

U.S. PATENT DOCUMENTS

| | | | |
|---|---|---|---|
| 5,403,312 A | 4/1995 | Yates et al. | |
| 5,485,947 A | 1/1996 | Olson et al. | |
| 6,978,921 B2 | 12/2005 | Shelton, IV et al. | |
| 7,000,818 B2 | 2/2006 | Shelton, IV et al. | |
| 7,401,721 B2 | 7/2008 | Holsten et al. | |
| 7,407,075 B2 | 8/2008 | Holsten et al. | |
| 7,422,139 B2 | 9/2008 | Shelton, IV et al. | |
| 7,464,849 B2 | 12/2008 | Shelton, IV et al. | |
| 7,669,746 B2 | 3/2010 | Shelton, IV | |
| 7,670,334 B2 | 3/2010 | Hueil et al. | |
| 7,735,703 B2 | 6/2010 | Morgan et al. | |

(Continued)

FOREIGN PATENT DOCUMENTS

| | | |
|---|---|---|
| CN | 105919642 A | 9/2016 |
| CN | 105997172 A | 10/2016 |

(Continued)

OTHER PUBLICATIONS

U.S. Food and Drug Administration 510(k) Premarket Notification, https://www.accessdata.fda.gov/scripts/cdrh/cfdocs/cfpmn/pmn.cfm?ID=K182476, last update: Jan. 8, 2024, 1 page.

*Primary Examiner* — Robert F Long

(57) ABSTRACT

A staple cartridge for use with a surgical stapling instrument is disclosed. The staple cartridge comprises a deck comprising a first staple cavity adjacent a longitudinal slot, a second staple cavity laterally and longitudinally offset relative to the first cavity, and a third staple cavity laterally and longitudinally offset relative to the second cavity. A first projection surrounds the first staple cavity, a second projection surrounds the second staple cavity, and a pair of third projections surrounds first and second portions of the third staple cavity, respectively. The first projection and the second projection are coupled together, and the second projection and one third projection are coupled together. The projections define a localized tissue-facing surface area. A localized valley is defined on the deck between the projections. The area of the localized valley area is greater than the localized tissue-facing area.

20 Claims, 7 Drawing Sheets

(56) References Cited

U.S. PATENT DOCUMENTS

| | | |
|---|---|---|
| 7,753,245 B2 | 7/2010 | Boudreaux et al. |
| 7,828,189 B2 * | 11/2010 | Holsten ............ A61B 17/07207 |
| | | 227/176.1 |
| 7,845,537 B2 | 12/2010 | Shelton, IV et al. |
| 7,980,443 B2 | 7/2011 | Scheib et al. |
| 8,123,100 B2 | 2/2012 | Holsten et al. |
| 8,141,762 B2 | 3/2012 | Bedi et al. |
| 8,210,411 B2 | 7/2012 | Yates et al. |
| 8,220,688 B2 | 7/2012 | Laurent et al. |
| 8,308,040 B2 | 11/2012 | Huang et al. |
| 8,393,514 B2 | 3/2013 | Shelton, IV et al. |
| 8,499,992 B2 | 8/2013 | Whitman et al. |
| 8,540,133 B2 | 9/2013 | Bedi et al. |
| 8,561,870 B2 | 10/2013 | Baxter, III et al. |
| 8,608,045 B2 | 12/2013 | Smith et al. |
| 8,733,613 B2 | 5/2014 | Huitema et al. |
| 8,864,007 B2 | 10/2014 | Widenhouse et al. |
| 8,876,857 B2 | 11/2014 | Burbank |
| 9,050,083 B2 | 6/2015 | Yates et al. |
| 9,072,535 B2 | 7/2015 | Shelton, IV et al. |
| 9,101,358 B2 | 8/2015 | Kerr et al. |
| 9,131,940 B2 | 9/2015 | Huitema et al. |
| 9,345,481 B2 | 5/2016 | Hall et al. |
| 9,386,988 B2 | 7/2016 | Baxter, III et al. |
| 9,629,631 B2 | 4/2017 | Nicholas et al. |
| 9,770,245 B2 | 9/2017 | Swayze et al. |
| 9,788,835 B2 | 10/2017 | Morgan et al. |
| 9,839,420 B2 | 12/2017 | Shelton, IV et al. |
| 9,844,369 B2 | 12/2017 | Huitema et al. |
| 9,924,944 B2 | 3/2018 | Shelton, IV et al. |
| 9,987,008 B2 | 6/2018 | Scirica |
| 10,080,552 B2 | 9/2018 | Nicholas et al. |
| 10,085,749 B2 | 10/2018 | Cappola et al. |
| 10,105,142 B2 | 10/2018 | Baxter, III et al. |
| 10,123,798 B2 | 11/2018 | Baxter, III et al. |
| 10,130,363 B2 | 11/2018 | Huitema et al. |
| 10,166,023 B2 | 1/2019 | Vendely et al. |
| 10,213,203 B2 | 2/2019 | Swayze et al. |
| 10,299,792 B2 | 5/2019 | Huitema et al. |
| 10,349,939 B2 | 7/2019 | Shelton, IV et al. |
| 10,357,252 B2 | 7/2019 | Harris et al. |
| 10,517,593 B2 | 12/2019 | Gupta et al. |
| 10,537,324 B2 | 1/2020 | Shelton, IV et al. |
| 10,542,981 B2 | 1/2020 | Miller et al. |
| 10,561,419 B2 | 2/2020 | Beardsley |
| 10,568,624 B2 | 2/2020 | Shelton, IV et al. |
| 10,568,652 B2 * | 2/2020 | Hess ............ A61B 17/320016 |
| 10,588,623 B2 | 3/2020 | Schmid et al. |
| 10,765,427 B2 | 9/2020 | Shelton, IV et al. |
| 10,898,183 B2 | 1/2021 | Shelton, IV et al. |
| 10,898,191 B2 | 1/2021 | Huitema et al. |
| 10,945,727 B2 | 3/2021 | Shelton, IV et al. |
| 10,952,724 B2 | 3/2021 | Shelton, IV et al. |
| 11,000,278 B2 | 5/2021 | Shelton, IV et al. |
| 11,045,191 B2 | 6/2021 | Shelton, IV et al. |
| 11,058,426 B2 | 7/2021 | Nalagatla et al. |
| D933,220 S | 10/2021 | Tate et al. |
| 11,147,552 B2 | 10/2021 | Burbank et al. |
| 11,207,065 B2 | 12/2021 | Harris et al. |
| 11,229,433 B2 | 1/2022 | Schings et al. |
| 11,234,698 B2 | 2/2022 | Shelton, IV et al. |
| 11,234,700 B2 | 2/2022 | Ragosta et al. |
| 11,266,409 B2 * | 3/2022 | Huitema ............ A61B 17/105 |
| 11,291,445 B2 | 4/2022 | Shelton, IV et al. |
| 11,298,129 B2 | 4/2022 | Bakos et al. |
| 11,337,693 B2 | 5/2022 | Hess et al. |
| 11,364,029 B2 | 6/2022 | Burbank et al. |
| 11,382,627 B2 | 7/2022 | Huitema et al. |
| D967,421 S | 10/2022 | Shelton, IV et al. |
| 11,490,890 B2 | 11/2022 | Harris et al. |
| 11,517,315 B2 | 12/2022 | Huitema et al. |
| D974,560 S | 1/2023 | Shelton, IV et al. |
| 11,540,826 B2 | 1/2023 | Nalagatla et al. |
| 11,571,213 B2 | 2/2023 | Huitema et al. |
| 11,589,865 B2 | 2/2023 | Shelton, IV et al. |
| 11,701,114 B2 | 7/2023 | Shelton, IV et al. |
| 11,737,752 B2 | 8/2023 | Schings et al. |
| 11,766,257 B2 | 9/2023 | Shelton, IV et al. |
| 11,826,047 B2 | 11/2023 | Huang et al. |
| 11,974,741 B2 | 5/2024 | Moubarak et al. |
| 2004/0004105 A1 * | 1/2004 | Jankowski ....... A61B 17/07207 |
| | | 227/176.1 |
| 2007/0175955 A1 | 8/2007 | Shelton et al. |
| 2013/0256373 A1 * | 10/2013 | Schmid ............ A61B 17/07207 |
| | | 227/176.1 |
| 2014/0001231 A1 | 1/2014 | Shelton, IV et al. |
| 2014/0263552 A1 | 9/2014 | Hall et al. |
| 2015/0134077 A1 | 5/2015 | Shelton, IV et al. |
| 2017/0367697 A1 * | 12/2017 | Shelton, IV ......... A61B 17/105 |
| 2018/0132849 A1 | 5/2018 | Miller et al. |
| 2018/0168615 A1 | 6/2018 | Shelton, IV et al. |
| 2019/0105047 A1 | 4/2019 | Nalagatla et al. |
| 2020/0054326 A1 * | 2/2020 | Harris .................. A61B 17/072 |
| 2020/0205811 A1 * | 7/2020 | Posey .................. A61B 17/072 |
| 2020/0405292 A1 * | 12/2020 | Shelton, IV ......... H01M 10/488 |
| 2021/0186490 A1 * | 6/2021 | Shelton, IV ..... A61B 17/07207 |
| 2021/0186494 A1 * | 6/2021 | Shelton, IV ......... A61B 17/072 |
| 2021/0186499 A1 * | 6/2021 | Shelton, IV ..... A61B 17/07207 |
| 2021/0186506 A1 * | 6/2021 | Shelton, IV ..... A61B 17/07207 |
| 2021/0290232 A1 * | 9/2021 | Harris ............... A61B 17/07207 |
| 2022/0031320 A1 | 2/2022 | Hall et al. |
| 2022/0047256 A1 | 2/2022 | Miller et al. |
| 2022/0047265 A1 | 2/2022 | Miller et al. |
| 2022/0296243 A1 * | 9/2022 | Nalagatla ................. A61L 31/10 |
| 2022/0304679 A1 | 9/2022 | Bakos et al. |
| 2022/0304680 A1 | 9/2022 | Shelton, IV et al. |
| 2022/0313264 A1 * | 10/2022 | Shelton, IV ............ A61L 31/10 |
| 2022/0346858 A1 | 11/2022 | Aronhalt et al. |
| 2022/0387027 A1 * | 12/2022 | Shelton, IV ..... A61B 17/07292 |
| 2023/0119119 A1 | 4/2023 | Moubarak |
| 2023/0309991 A1 * | 10/2023 | Schings ............... A61B 17/068 |
| | | 227/181.1 |

FOREIGN PATENT DOCUMENTS

| | | | |
|---|---|---|---|
| CN | 105997173 A | 10/2016 | |
| CN | 106036848 A | 10/2016 | |
| CN | 108542454 A | 9/2018 | |
| CN | 111195142 A | 5/2020 | |
| EP | 2932918 A1 * | 10/2015 | ......... A61B 17/0644 |

* cited by examiner

STAPLE CARTRIDGES COMPRISING STAPLE RETENTION FEATURES

BACKGROUND

The present invention relates to surgical staple cartridges configured for use with surgical stapling instruments designed to staple and cut tissue.

SUMMARY

A staple cartridge for use with a surgical stapling instrument is disclosed. The staple cartridge comprises a cartridge body comprising a longitudinal slot and a deck defining a local deck area. The deck comprises a first staple cavity adjacent the longitudinal slot, a second staple cavity laterally and longitudinally offset relative to the first cavity, and a third staple cavity laterally and longitudinal offset relative to the second cavity and laterally offset and longitudinally aligned with the first staple cavity. The deck further comprises a first projection extending therefrom surrounding a portion of the first staple cavity, a second projection extending therefrom surrounding a portion of the second staple cavity, and a pair of third projections extending therefrom surrounding first and second portions of the third staple cavity, respectively. The first projection and the second projection are coupled together, and the second projection and the one third projection are coupled together. The first projection, the second projection, and the pair of third projections define a localized tissue-facing surface area. A localized valley having a localized valley area is defined on the deck between the first projection, the second projection, and the pair of third projections. The localized valley area is greater than the localized tissue-facing area.

LISTING OF THE DRAWINGS

Various features of the embodiments described herein, together with advantages thereof, may be understood in accordance with the following description taken in conjunction with the accompanying drawings as follows.

Corresponding reference characters indicate corresponding parts throughout the several views.

DETAILED DESCRIPTION

Figure 1:
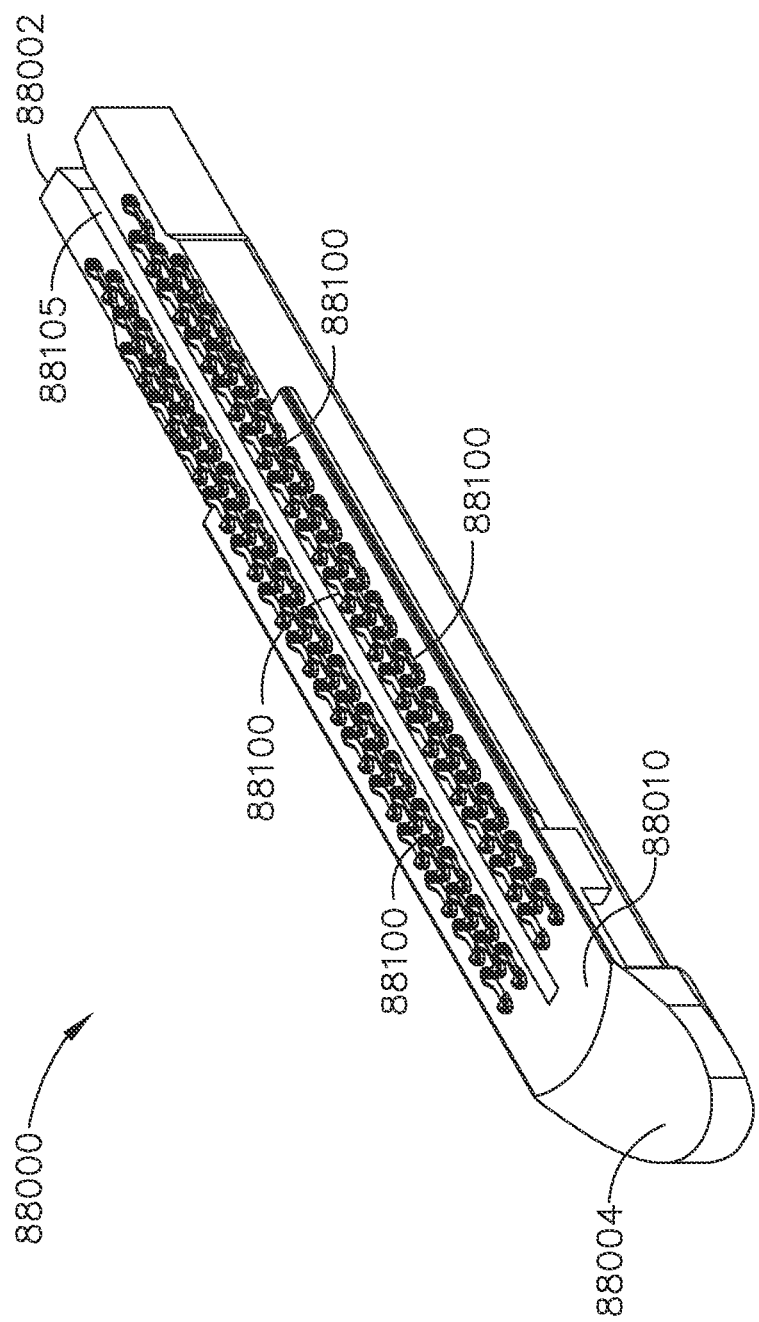
FIG. 1 is a perspective view of a staple cartridge for use with a surgical stapling instrument in accordance with the present disclosure.

Applicant of the present application owns the following U.S. Patent Applications that were filed on Oct. 13, 2023, and which are each herein incorporated by reference in their respective entireties:

U.S. patent application Ser. No. 18/379,759, titled METHOD OF OPERATING A SURGICAL STAPLING INSTRUMENT;

U.S. patent application Ser. No. 18/379,762, titled SURGICAL STAPLING SYSTEMS WITH ADAPTIVE STAPLE FIRING ALGORITHMS;

U.S. patent application Ser. No. 18/379,763, titled LEARNED TRIGGERS FOR ADAPTIVE CONTROL OF SURGICAL STAPLING SYSTEMS;

U.S. patent application Ser. No. 18/379,766, titled CONTROL CIRCUIT FOR ACTUATING MOTORIZED FUNCTION OF SURGICAL STAPLING INSTRUMENT UTILIZING INERTIAL DRIVE TRAIN PROPERTIES;

U.S. patent application Ser. No. 18/379,768, titled PROPORTIONATE BALANCING OF THE FUNCTION IMPACT MAGNITUDE OF BATTERY OUTPUT TO PEAK MOTOR CURRENT;

U.S. patent application Ser. No. 18/379,771, titled MOTOR OPTIMIZATION BY MINIMIZATION OF PARASITIC LOSSES AND TUNING MOTOR DRIVE CONFIGURATION;

U.S. patent application Ser. No. 18/379,773, titled APPARATUS AND METHOD TO REDUCE PARASITIC LOSSES OF THE ELECTRICAL SYSTEM OF A SURGICAL INSTRUMENT;

U.S. patent application Ser. No. 18/379,776, titled SURGICAL TOOL WITH RELAXED FLEX CIRCUIT ARTICULATION;

U.S. patent application Ser. No. 18/379,777, titled WIRING HARNESS FOR SMART STAPLER WITH MULTI AXIS ARTICULATION;

U.S. patent application Ser. No. 18/379,781, titled SURGICAL SYSTEM WITH WIRELESS ARRAY FOR POWER AND DATA TRANSFER; and U.S. patent application Ser. No. 18/379,784, titled SURGICAL STAPLE CARTRIDGE COMPRISING REPLACEABLE ELECTRONICS PACKAGE;

Applicant of the present application owns the following U.S. Patent Applications that were filed on Oct. 13, 2023, and which are each herein incorporated by reference in their respective entireties:

U.S. patent application Ser. No. 18/379,790, titled METHOD OF ASSEMBLING A STAPLE CARTRIDGE;

U.S. patent application Ser. No. 18/379,793, titled CONTROL SURFACES ON A STAPLE DRIVER OF A SURGICAL STAPLE CARTRIDGE;

U.S. patent application Ser. No. 18/379,796, titled INTEGRAL CARTRIDGE STIFFENING FEATURES TO REDUCE CARTRIDGE DEFLECTION;

U.S. patent application Ser. No. 18/379,801, titled STAPLE CARTRIDGE COMPRISING WALL STRUCTURES TO REDUCE CARTRIDGE DEFLECTION;

U.S. patent application Ser. No. 18/379,803, titled PANLESS STAPLE CARTRIDGE ASSEMBLY COM-

PRISING RETENTION FEATURES FOR HOLDING STAPLE DRIVERS AND SLED;

U.S. patent application Ser. No. 18/379,805, titled STAPLE CARTRIDGE COMPRISING A SLED HAVING A DRIVER LIFT CAM;

U.S. patent application Ser. No. 18/379,808, titled SURGICAL STAPLE CARTRIDGES WITH SLEDS CONFIGURED TO BE COUPLED TO A FIRING DRIVER OF A COMPATIBLE SURGICAL STAPLER;

U.S. patent application Ser. No. 18/379,810, titled STAPLE CARTRIDGE COMPRISING A COMPOSITE SLED;

U.S. patent application Ser. No. 18/379,811, titled SURGICAL INSTRUMENTS WITH JAW AND FIRING ACTUATOR LOCKOUT ARRANGEMENTS LOCATED PROXIMAL TO A JAW PIVOT LOCATION;

U.S. patent application Ser. No. 18/379,815, titled SURGICAL INSTRUMENTS WITH LATERALLY ENGAGEABLE LOCKING ARRANGEMENTS FOR LOCKING A FIRING ACTUATOR;

U.S. patent application Ser. No. 18/379,817, titled DUAL INDEPENDENT KEYED LOCKING MEMBERS ACTING ON THE SAME DRIVE MEMBER;

U.S. patent application Ser. No. 18/379,820, titled ADJUNCTS FOR USE WITH SURGICAL STAPLING INSTRUMENTS;

U.S. patent application Ser. No. 18/379,822, titled ADJUNCTS FOR USE WITH SURGICAL STAPLING INSTRUMENTS;

U.S. patent application Ser. No. 18/379,826, titled JAW CONTROL SURFACES ON A SURGICAL INSTRUMENT JAW;

U.S. patent application Ser. No. 18/379,827, titled ZONED ALGORITHM ADAPTIVE CHANGES BASED ON CORRELATION OF COOPERATIVE COMPRESSION CONTRIBUTIONS OF TISSUE; and U.S. patent application Ser. No. 18/379,831, titled STAPLE CARTRIDGES COMPRISING TRACE RETENTION FEATURES.

Numerous specific details are set forth to provide a thorough understanding of the overall structure, function, manufacture, and use of the embodiments as described in the specification and illustrated in the accompanying drawings. Well-known operations, components, and elements have not been described in detail so as not to obscure the embodiments described in the specification. The reader will understand that the embodiments described and illustrated herein are non-limiting examples, and thus it can be appreciated that the specific structural and functional details disclosed herein may be representative and illustrative. Variations and changes thereto may be made without departing from the scope of the claims.

The terms "proximal" and "distal" are used herein with reference to a clinician manipulating the handle portion of the surgical instrument. The term "proximal" refers to the portion closest to the clinician and the term "distal" refers to the portion located away from the clinician. It will be further appreciated that, for convenience and clarity, spatial terms such as "vertical", "horizontal", "up", and "down" may be used herein with respect to the drawings. However, surgical instruments are used in many orientations and positions, and these terms are not intended to be limiting and/or absolute.

Various exemplary devices and methods are provided for performing laparoscopic and minimally invasive surgical procedures. However, the reader will readily appreciate that the various methods and devices disclosed herein can be used in numerous surgical procedures and applications including, for example, in connection with open surgical procedures. As the present Detailed Description proceeds, the reader will further appreciate that the various instruments disclosed herein can be inserted into a body in any way, such as through a natural orifice, through an incision or puncture hole formed in tissue, etc. The working portions or end effector portions of the instruments can be inserted directly into a patient's body or can be inserted through an access device that has a working channel through which the end effector and elongate shaft of a surgical instrument can be advanced.

A surgical stapling system can comprise a shaft and an end effector extending from the shaft. The end effector comprises a first jaw and a second jaw. The first jaw comprises a staple cartridge. The staple cartridge is insertable into and removable from the first jaw; however, a staple cartridge may not be removable from, or at least readily replaceable from, the first jaw. The second jaw comprises an anvil configured to deform staples ejected from the staple cartridge. The second jaw is pivotable relative to the first jaw about a closure axis; however, the first jaw may be pivotable relative to the second jaw. The surgical stapling system further comprises an articulation joint configured to permit the end effector to be rotated, or articulated, relative to the shaft. The end effector is rotatable about an articulation axis extending through the articulation joint. However, the surgical stapling system may not include an articulation joint.

The staple cartridge comprises a cartridge body. The cartridge body includes a proximal end, a distal end, and a deck extending between the proximal end and the distal end. In use, the staple cartridge is positioned on a first side of the tissue to be stapled and the anvil is positioned on a second side of the tissue. The anvil is moved toward the staple cartridge to compress and clamp the tissue against the deck. Thereafter, staples removably stored in the cartridge body can be deployed into the tissue. The cartridge body includes staple cavities defined therein wherein staples are removably stored in the staple cavities. The staple cavities are arranged in six longitudinal rows. Three rows of staple cavities are positioned on a first side of a longitudinal slot and three rows of staple cavities are positioned on a second side of the longitudinal slot. Other arrangements of staple cavities and staples may be possible.

The staples are supported by staple drivers in the cartridge body. The drivers are movable between a first, or unfired position, and a second, or fired, position to eject the staples from the staple cavities. The drivers are retained in the cartridge body by a retainer which extends around the bottom of the cartridge body and includes resilient members configured to grip the cartridge body and hold the retainer to the cartridge body. The drivers are movable between their unfired positions and their fired positions by a sled. The sled is movable between a proximal position adjacent the proximal end and a distal position adjacent the distal end. The sled comprises a plurality of ramped surfaces configured to slide under the drivers and lift the drivers, and the staples supported thereon, toward the anvil.

Further to the above, the sled is moved distally by a firing driver. The firing driver is configured to contact the sled and push the sled toward the distal end. The longitudinal slot defined in the cartridge body is configured to receive the firing driver. The anvil also includes a slot configured to receive the firing driver. The firing driver further comprises a first cam which engages the first jaw and a second cam which engages the second jaw. As the firing driver is advanced distally, the first cam and the second cam can control the distance, or tissue gap, between the deck of the staple cartridge and the anvil. The firing driver also comprises a knife configured to incise the tissue captured intermediate the staple cartridge and the anvil. It is desirable for the knife to be positioned at least partially proximal to the ramped surfaces such that the staples are ejected ahead of the knife.

Surgical stapling devices are commonly used in a variety of different surgical procedures to staple or otherwise fasten incised tissue. Such devices include an end effector that comprises a pair of jaws that are movable between an open position and closed positions. An elongate shaft is coupled to the end effector that facilitates insertion of the end effector into the patient, oftentimes through a cannula of a trocar or other constricted opening. The shaft may be coupled to a handle, or housing, that facilitates manual actuation of the end effector or the handle may comprise a motor or motors for applying actuation motions to the end effector. In alternative arrangements, the shaft may operably interface with a robotic system which is configured to manipulate the shaft and apply actuation motions to the end effector.

The shaft facilitates the transfer of opening and closing motions to the pair of jaws. A surgical staple cartridge is mounted in one of the jaws that comprises a channel and the other, opposing jaw comprises an anvil. The channel can be movable toward the anvil during a closure stroke. The anvil can be movable toward the channel during the closure stroke; however it is envisioned that both the anvil and the channel can move toward each other during the closure stroke. The surgical staple cartridge commonly comprises a cartridge body that defines a deck surface oriented to face an underside of the anvil. Lines of surgical staples are received on staple drivers that are movably mounted in corresponding staple cavities formed in the cartridge body that open through the deck surface.

The end effector further includes a sled driver, or firing member or firing actuator, that is formed with camming surfaces or is configured to cooperate with a sled that includes camming surfaces or ramps configured to drive the staple drivers upward in the staple cavities. The sled driver may additionally be provided with other camming members or guide tabs configured to slidably engage the anvil and the channel to retain the anvil at a proper spacing relative to the staple cartridge during the firing process. This spacing between the underside or forming surface of the anvil and the deck of the staple cartridge is often referred to as the "tissue gap." The sled driver in those end effectors that are designed to cut tissue as well as staple or fasten tissue is equipped with a knife, or tissue cutting blade or surface. The knife, or tissue cutting blade can be provided separate from the sled driver. The shaft accommodates a movable firing beam or other known arrangement configured to drive the sled driver distally through the staple cartridge and retract the sled driver after the cutting and stapling procedure is completed.

The cartridge body is formed with a longitudinal slot that is configured to accommodate travel of the sled driver through the cartridge. The staple cavities open through the deck surface and are arranged to form an orientation of offset longitudinal rows on each side of the longitudinal slot. The staple cavities movably store staples therein. In use, the end effector is positioned around a patient tissue to be cut and stapled ("target tissue") with the jaws in the open position to enable the target tissue to be positioned between the underside of the anvil and the cartridge deck. The anvil can be moved toward the channel and/or the channel can be moved toward the anvil to motivate the end effector into the closed position. Once the target tissue has been desirably positioned between the anvil and the staple cartridge, the end effector is moved to a fully-closed position thereby clamping the target tissue between the anvil and the cartridge. Thereafter, the firing beam, firing bar, or other actuator arrangement is actuated to advance the sled driver and the sled distally through the cartridge. As the sled moves distally, the camming surfaces thereon sequentially cam the staple drivers upward in the staple cavities causing the staples temporarily supported on the staple drivers to pass through the clamped tissue and into forming contact with the underside of the anvil. The knife or cutting blade lags behind the sled, ensuring that the lines of staples are formed before the clamped tissue is incised.

A cartridge jaw, or channel, of a surgical instrument end effector is sized to receive a cartridge of a particular size. However, it is oftentimes desirable to use different staple types, or sizes, during a particular surgical procedure. Stated another way, different staples are preferable for use with different tissues and/or for different tissue sealing outcomes. In an effort to reduce the surgical instruments used during the surgical procedure, it is desirable to have a universally-sized staple cartridge that fits in a single cartridge jaw that is capable of storing staples of different sizes and/or geometries. Differences in staples include, for example, composition material, staple leg diameter, and/or staple length, for example.

FIG. 1 depicts a staple cartridge 88000 that is seatable in a cartridge jaw of an end effector. In use, the staple cartridge 88000 can be readily seated into the cartridge jaw during a surgical procedure, fired, and then removed from the cartridge jaw so that the now-spent staple cartridge 88000 can be replaced with another staple cartridge. That said, the staple cartridge 88000 may not be readily removable from the cartridge jaw and is not replaceable during a surgical procedure. The staple cartridge 88000 comprises a cartridge body including a deck surface 88010 configured to oppose an anvil of the end effector when the staple cartridge 88000 is seated in the cartridge jaw and the end effector is moved into a closed configuration. Staple cavities 88100 are defined in the cartridge body of the staple cartridge 88000 that are each configured to receive and store a staple therein. The staple cavities 88100 are arranged in six longitudinal rows, with three longitudinal rows on each side of a longitudinal slot 88005 defined in the cartridge body. The longitudinal rows of staple cavities extend between a proximal end 88002 and a distal end 88004 of the staple cartridge 88000. Alternatively, any suitable number of staple cavity rows and/or staple cavities is envisioned and can be selected based on the needs of a particular surgical procedure, for example.

The longitudinal slot 88005 extends between the proximal end 88002 and the distal end 88004 of the staple cartridge 88000 and is sized to receive a firing driver, or firing actuator, to eject staples out of the staple cartridge 88000 during a staple firing stroke. Various aspects of staple cartridges are described in greater detail in U.S. Pat. No. 9,844,369. The entire disclosure of U.S. Pat. No. 9,844,369, entitled SURGICAL END EFFECTORS WITH FIRING ELEMENT MONITORING ARRANGEMENTS, which issued on Dec. 19, 2017, is incorporated by reference herein.

Figure 2:
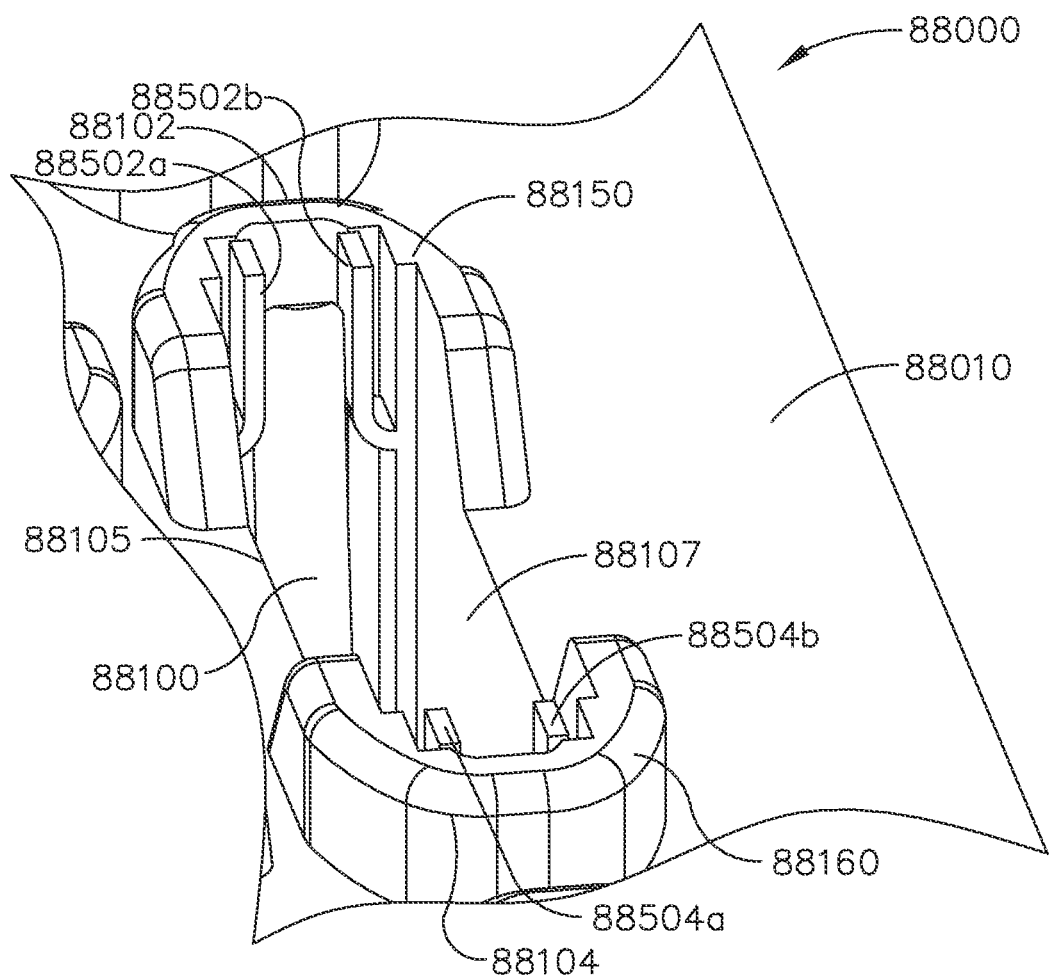
FIG. 2 is a partial perspective view of the staple cartridge of FIG. 1 comprising a staple cavity and staple retention features configured to maintain alignment of a staple within the staple cavity.

Referring now to FIG. 2, an enlarged view of a staple cavity 88100 defined in the staple cartridge 88000 is depicted. The staple cavity 88100 shown in FIG. 2 is representative of all staple cavities defined in the staple cartridge 88000. All of the staple cavities defined in the staple cartridge can comprise the same features, whereas only a select number of staple cavities may comprise the same features. For example, features of the staple cavities can vary laterally amongst the longitudinal rows or can vary longitudinally across the staple cartridge 88000.

The staple cavity 88100 comprises a proximal end 88102 and a distal end 88104. A first lateral wall 88105 and a second lateral wall 88107 span between the proximal and distal ends 88102, 88104. The first lateral wall 88105 extends along a first side of the staple cavity 88100, whereas the second lateral wall 88107 extends along a second side of the staple cavity 88100 opposite of the first side.

A staple is movably stored in the staple cavity 88100. A first pocket extender, or projection, 88150 extends a first distance from the deck surface 88010 of the staple cartridge 80000, and a second pocket extender, or projection 88160 extends a second distance from the deck surface 88010 of the staple cartridge 80000. The first distance of the first pocket extender 88150 is the same as the second distance of the second pocket extender 88160; however, the first distance and the second distance may not be the same. The first projection 88150 surrounds at least a portion of the proximal end 88102 of the staple cavity 88100, and the second projection 88160 surrounds at least a portion of the distal end 88104 of the staple cavity 88100. While the first projection 88150 and the second projection 88160 are shown in FIG. 2 as being discrete, or independent, from one another, the first projection 88150 and the second projection 88160 can be coupled, or otherwise connected to one another.

Figure 3:
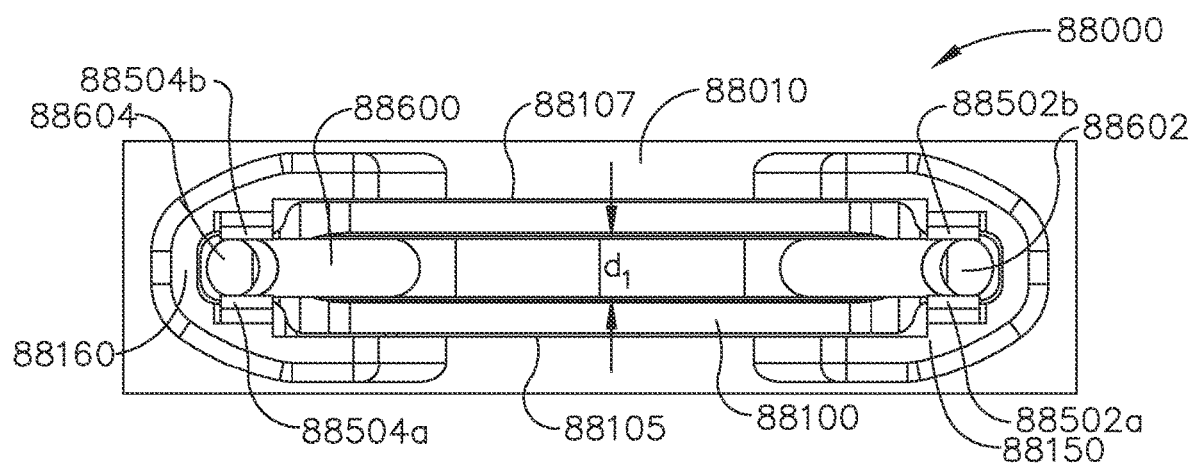
FIG. 3 is a plan view of the staple cavity of FIG. 2 with a first staple stored therein.

As discussed above, each staple cavity 88100 is configured to store a staple therein. Referring to FIG. 3, a staple 88600 is positioned in the staple cavity 88100. The staple 88600 is comprised of a metal wire, such as stainless steel, for example, and comprises a base, a first leg 88602 extending from a first end of the base, and a second leg 88604 extending from a second, or opposite, end of the base. During the staple firing stroke, a staple driver of the staple cartridge 88000 is pushed upwardly within the staple cavity 88100 which contacts the base of the staple 88600 and pushes the staple 88600 upwardly from an unfired position to a fired position. As such, the tips of the staple legs 88602, 88604 come into contact with an anvil positioned opposite the staple cartridge 88000 and the staple 88600 is deformed from an unfired configuration, such as a V-shaped configuration, for example, into a fired configuration, such as a B-shaped configuration, for example. The staple 88600 can comprise any suitable height when it is in its unfired configuration. For instance, the staple 88600 can comprise an unfired height of approximately 3.0 mm, approximately 4.0 mm, or approximately 5.0 mm, for example. Depending on the height of the staple 88600, the tips of the staple 88600 may be recessed with respect to, flush with, or extend above the deck surface 88010 when the staple 88600 is in its unfired position. In any one of these arrangements, the first and second projections 88150 and 88160 can prevent, or at least reduce the possibility of, the staple tips from snagging on patient tissue and/or being damaged or disturbed within the staple cavity 88100. Moreover, the first and second projections 88150, 88160 provide additional support, or guidance, to the staple 88600 to maintain the staple 88600 in a desired alignment, or orientation, as the staple 88600 is lifted out of the staple cartridge 88000 toward the opposing anvil during the staple firing stroke.

As described herein, it is desirable for a cartridge body of a staple cartridge to be compatible with, or able to be used with, staples of varying sizes and/or geometries. For instance, as described above, staples can have different unformed heights and it may be desirable for the staple cavities of a cartridge body to be able to receive short staples or tall staples. Also, for instance, wire staples can have different diameters and, similar to the above, it is desirable for the staple cavities of a cartridge body to be able to receive staples having a thick diameter or a thin diameter. To achieve this, the staple cavities of a staple cartridge must be configured appropriately to receive a variety of staples therein. Stated another way, the staple cavities must be large enough to accommodate receiving a thick wire staple, while also being able to receive a thin wire staple, for example. More specifically, as shown in FIGS. 3-6, the staple cartridge 88000 can be used with staples having different diameters. The staple cartridge 88000 can be used with first staples 88600 having a first diameter $d_1$ of 0.0096 inches, for example. The staple cartridge 88000 can also be used with second staples 88600' having a second diameter $d_2$ of 0.0079 inches, for example. The second diameter $d_2$ is less than the first diameter $d_1$.

Regardless of the size and/or shape of the staple movably stored in the staple cavity, it may be desirable for the staple to be centered within the staple cavity for optimal staple firing and/or formation. It may be desirable for the staple to be positioned equidistant from the first lateral wall 88105 and the second lateral wall 88107 of the staple cavity 88100 and in an upright orientation. The reader should appreciate that the first and second lateral sidewalls 88105 and 88107 may be not be perfectly straight or planar owing to manufacturing variations, for instance. As such, the center of a staple cavity 88100 may be approximated by an average midpoint measured laterally between the first and second lateral sidewalls 88105 and 88107 along the longitudinal length of the staple cavity 88100. Moreover, along these lines, the staple positioned in the staple cavity 88100 need not be perfectly centered between the first and second lateral sidewalls 88105 and 88107 in order for the staple to be equidistant between the first and second lateral sidewalls 88105 and 88107. For instance, the longitudinal center plane of a staple can be shifted laterally—in either lateral direction—up to 25% of the lateral width of the staple relative to the longitudinal center plane of the staple cavity 88100, for example, for the staple to be positioned equidistant between the first and second lateral sidewalls 88105 and 88107. Similarly, the reader should appreciate that a staple may also not be straight or planar owing to manufacturing variations. As such, similar to the above, the longitudinal center plane of a staple may be approximated by an average midpoint measured laterally between the first and second lateral sides of the staple. A staple can be sufficiently equidistant between the first lateral wall 88105 and the second lateral wall 88107 if the staple tips are properly aligned with, or registered with, the forming pockets defined in the anvil positioned opposite the staple cartridge 88000.

Figure 4:
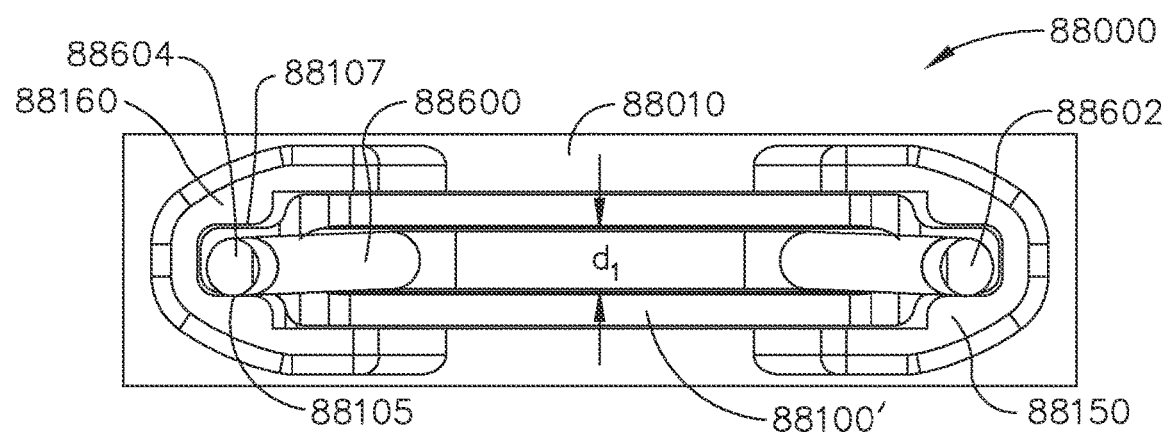
FIG. 4 is a plan view of a staple cavity lacking the staple retention features of FIG. 2 with the first staple of FIG. 3 stored therein.
Figure 6:
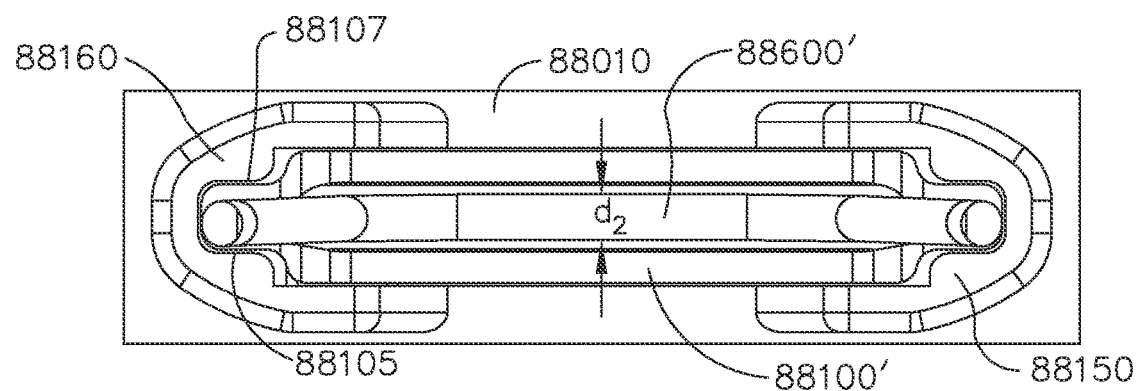
FIG. 6 is a plan view of the staple cavity of FIG. 4 with the second staple of FIG. 5 stored therein.

As shown in FIG. 6, placement of the second staples 88600' having a smaller diameter into the universal staple cavities 88100' of a staple cartridge 88000', without additional structure, results in the second staples 88600' being haphazardly stored in the staple cavities 88100'. Such loose, non-uniform storage of second staples can result in the creation of a non-uniform staple line, for example. The second staples 88600' may not remain centered in the universal staple cavities 88100' and, as such, the second staples 88600' may have unintended angular offset when ejected during the staple firing stroke. Such angular offset can result in the second staples failing to strike the appropriate forming pockets defined in the opposing anvil, leading to increased staple malformations. Placement of the first staples 88600 having a larger diameter into the universal staple cavities 88100' of the staple cartridge 88000', without additional structure, can also lead to the first staples 88600 being off-center, as shown in FIG. 4. For example, first and second legs 88604, 88604 of the first staple 88600 can be tilted toward and/or rested against the first lateral wall 88105 of the staple cavity 88100'. The legs of an uncentered staple can gouge into the sidewalls of a staple cavity which can prevent the staple from being ejected from the staple cavity.

In an effort to ensure the proper alignment of a staple within a universal staple cavity 88100, the staple cavity 88100 comprises one or more staple alignment features 88502, 88504 integrally formed with the body of the staple cartridge 88000. As shown in FIG. 2, the staple alignment features 88502, 88504 are integrally-formed with the first lateral wall 88105 and the second lateral wall 88107 of the staple cavity 88100. The staple alignment features 88502, 88504 comprise spring tabs, or arms, but can comprise any suitable configuration. A first pair of spring tabs 88502a, 88502b extend into the staple cavity 88100 from the first lateral wall 88105 and the second lateral wall 88107, respectively, at a proximal portion of the staple cavity 88100. A second pair of spring tabs 88504a, 88504b extend into the staple cavity 88100 from the first lateral wall 88105 and the second lateral wall 88107, respectively, at a distal portion of the staple cavity 88100. The spring tabs 88502, 88504 are configured to bias against, or otherwise contact, first and second legs 88602, 88604 of the staple, respectively, while the staple is movably stored in the staple cavity 88100. Such engagement between the spring tabs 88502, 88504 and the staple legs 88602, 88604 serves to maintain the staple 88600, for instance, in a centered orientation within the staple cavity 88100.

Figure 5:
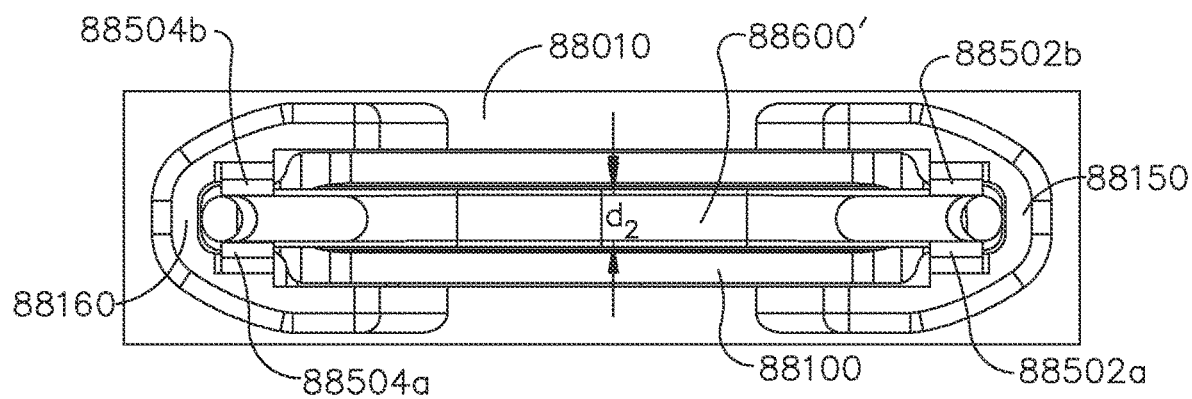
FIG. 5 is a plan view of the staple cavity of FIG. 2 with a second staple stored therein.

As shown in FIGS. 3 and 5, the spring tabs 88502, 88504 are configured to maintain the staple in a centered, upright orientation within the staple cavity 88100 regardless of the staple's diameter and/or geometry. Due to their resilient nature, the spring tabs 88502, 88504 are configured to be biased toward the first lateral wall 88105 and the second lateral wall 88107 to different degrees based at least in part on the diameter of the staple movably stored therein. FIG. 2 depicts the spring tabs 88502, 88504 in their unbiased, or natural, configuration as no staple is present in the staple cavity 88100. A distance spanning between the pair of spring tabs 88502a, 88502b is referred to herein as a staple gap width. The smallest staple diameter compatible for use with the staple cartridge 88000 can be a diameter equal to the staple gap width when the spring tabs 88502a, 88502b are in their unbiased configuration. Conversely, the largest staple diameter compatible for use with the staple cartridge 88000 is a diameter equal to the staple gap width when the spring tabs 88502a, 88502b are in their fully-biased configuration, i.e., the spring tabs 88502a, 88502b biased against the first lateral wall 88105 and the second lateral wall 88107, respectively.

As shown in FIG. 5, the staple cavity 88100 movably stores the second staple 88600' having a diameter $d_2$ smaller than the diameter $d_1$ of the first staple 88600 shown stored in the staple cavity 88100 in FIG. 3. As such, the spring tabs 88502, 88504 remain closer to their unbiased configuration to make sufficient contact with the staple 88600' to maintain the staple 88600' in a centered, upright orientation. If the staple comprises a larger diameter, as shown in FIG. 3, the spring tabs 88502, 88504 are biased closer to the first lateral wall 88105 and the second lateral wall 88107, respectively, to accommodate for the larger diameter $d_1$ of the first staple 88600.

While the staple alignment features 88502, 88504 are depicted as arms in the form of spring tabs, any suitable resilient member, such as a spring, a layer of foam, and/or other resilient material, for example, is envisioned. Furthermore, the staple alignment features 88502, 88504 extend a depth into the staple cavities sufficient to support staples having varying staple leg lengths that are suitable, or otherwise desirable, for use with the staple cartridge 88000. While the staple alignment features 88502, 88504 are depicted as being positioned on both lateral side walls of the staple cavity and at both proximal and distal ends of the staple cavity, any position and/or quantity of staple alignment features are envisioned that are suitable to support, or otherwise accommodate staples of different diameters.

As described above, the staple alignment features 88502, 88504 are in contact with a staple positioned in the staple cavity 88100 to position the staple within the staple cavity 88100. As also described above, each alignment feature 88502, 88504 is configured to apply a force to the staple. Such forces can act normally or perpendicularly to surface of the staple and, when the staple is ejected from the staple cavity 88100 during the staple firing stroke, friction forces between the alignment features 88502, 88504 resist, but do not prevent, the ejection of the staple from the staple cavity 88100. The magnitude of the friction forces are proportional to the magnitude of the forces applied to the staple by the alignment features 88502, 88504. Such an arrangement advantageously retains, i.e., releasably retains, the staple in the staple cavity 88100 and prevents, or at least reduces the possibility of, the staple from accidentally falling out of the staple cavity 88100. The alignment features 88502, 88504 may hold the staple in position without the staple touching any other part of the staple cavity 88100. The staple may be in contact with one or more walls of the staple cavity 88100 in addition to being in contact with the alignment features 88402, 88504. As such, the staple is substantially V-shaped and the legs of the staple are in contact with the proximal and distal end walls of the staple cavity 88100.

As discussed above, one or more of the projections of the staple cartridge 88000 extend a staple cavity above the deck surface 88010. For instance, the first projection 88150 and the second projection 88160 extend a staple cavity 88100 above the deck surface 88010. As the staple stored in the staple cavity 88100 is ejected, or fired, during a staple firing actuation, the legs of the staple are supported by the projections 88150 and 88160 when the staple legs emerge above the deck surface 88010. A, the possibility of the staple legs becoming misaligned with the staple forming pockets defined in the anvil is reduced. Further to the below, referring to FIGS. 7-9, projections 89110, 89210, and 89310 also comprise staple cavity extenders.

As discussed further below, it is desirable to maintain the tissue captured between the jaws of the end effector in position during the staple firing stroke to optimize the sealing and cutting of the tissue. It may be desirable to hold the tissue positioned adjacent the longitudinal slot of the cartridge body as this tissue may experience the greatest displacement forces during the staple firing stroke owing to the firing driver translating distally through the longitudinal slot. Such displacement forces tend to lead to rippling and/or bunching of the tissue that can result in a non-uniform staple formation line and/or an ineffective seal along the cut line, for example. Moreover, while projections extending from the cartridge deck can be used to hold the tissue in position, such projections can create stress and strain within the tissue and, as discussed in greater detail below, the projections can be configured to alleviate or reduce the stress and strain within the tissue.

Figure 7:
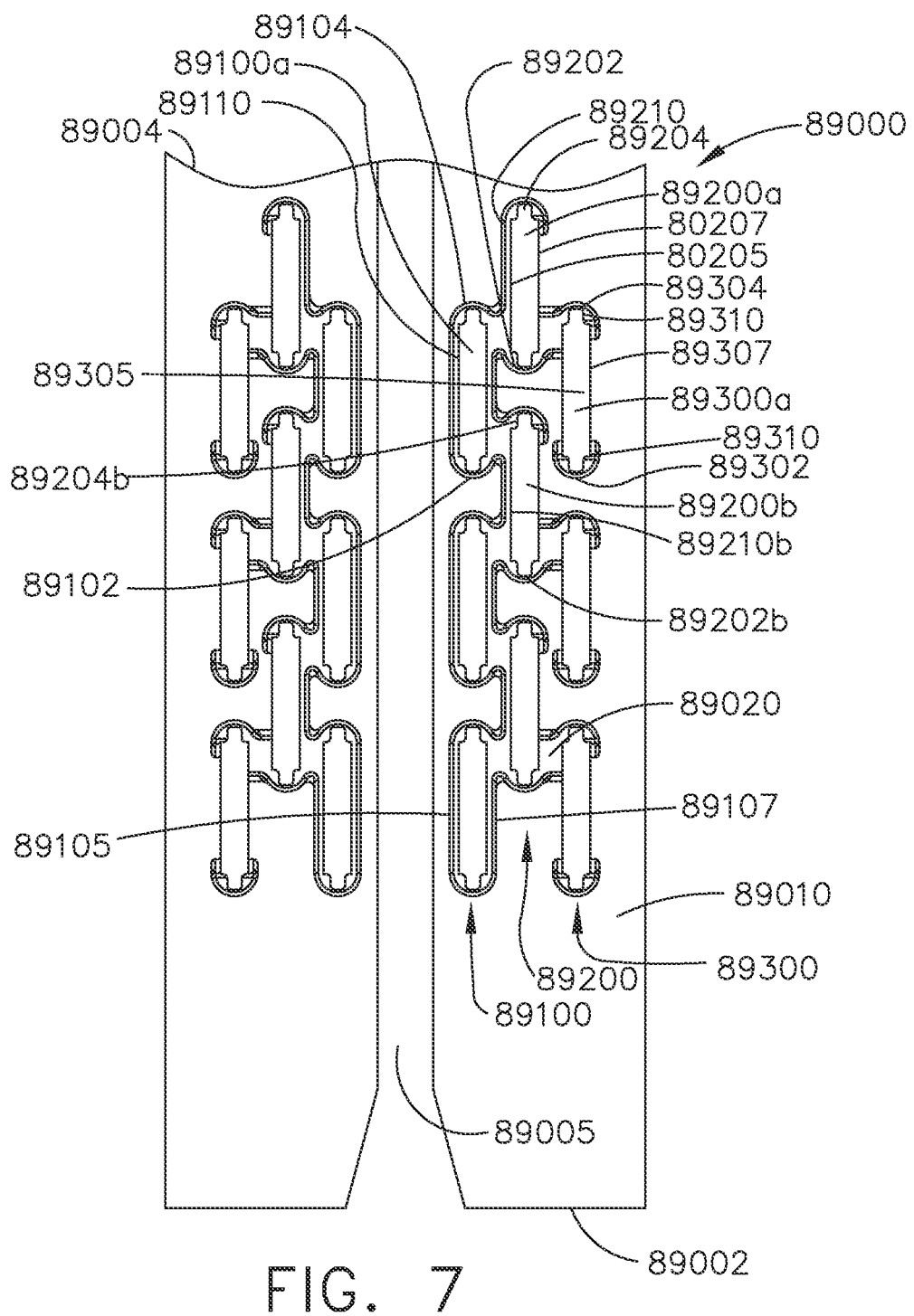
FIG. 7 is a partial plan view of a staple cartridge for use with a surgical stapling instrument in accordance with the present disclosure, wherein the staple cartridge comprises projections extending from a deck surface.
Figure 8:
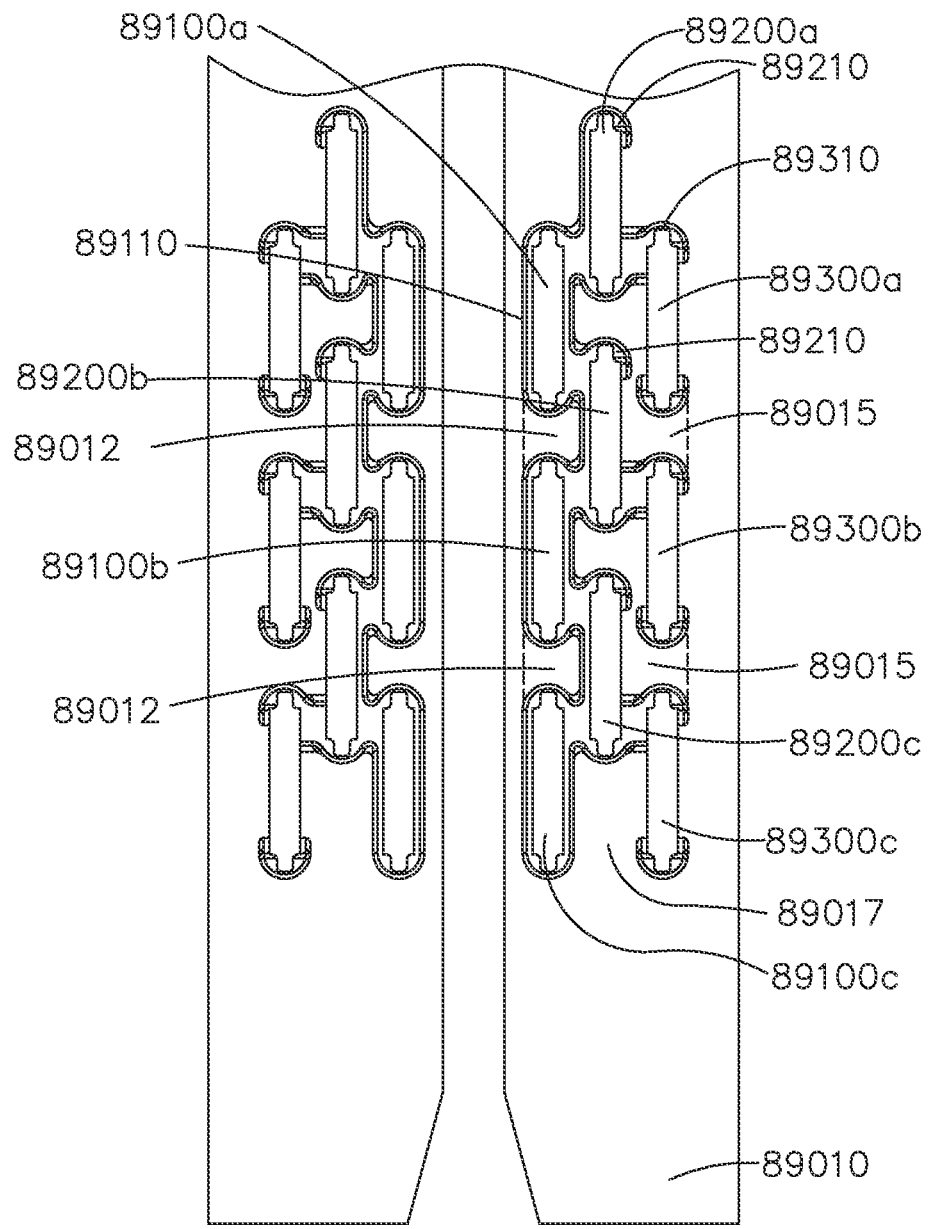
FIG. 8 is a partial plan view of the staple cartridge of FIG. 7.

Referring to FIGS. 7 and 8, a staple cartridge 89000 comprises a cartridge body including a deck surface 89010. A longitudinal slot 89005 is defined in the cartridge body and extends from a proximal end 89002 toward a distal end 89004 of the staple cartridge 89000. The longitudinal slot 89005 is sized to accommodate the travel of a firing driver through the staple cartridge 89000 during a staple firing stroke.

Staple cavities are defined in the staple cartridge 89000 and are arranged in six longitudinal rows. Three longitudinal rows of staple cavities are defined on a first side of the longitudinal slot 89005, and three longitudinal rows of staple cavities are defined on a second side of the longitudinal slot 89005. The arrangement of staple cavities on the first side is mirrored across the longitudinal slot 89005 onto the second side of the staple cartridge 89000. Alternatively, any suitable arrangement of staple cavities can be used. As shown in FIGS. 7 and 8, a first longitudinal row of staple cavities 89100 extends alongside the longitudinal slot 89005, a second longitudinal row of staple cavities 89200 extends alongside the first longitudinal row of staple cavities 89100, and a third longitudinal row of staple cavities 89300 extends alongside the second longitudinal row of staple cavities 89200. The first, second, and third longitudinal rows of staple cavities 89100, 89200, 89300 are defined on a first side of the longitudinal slot 89005.

A staple cavity from the first longitudinal row of staple cavities 89100 comprises a corresponding first projection 89110 extending from the deck surface 89010. Each first projection 89110 surrounds the staple cavity 89100 from the first longitudinal row to a first degree. Stated another way, each first projection 89110 surrounds a first length of a perimeter of a staple cavity 89100 from the first longitudinal row. As shown in FIG. 7, the first projection 89110 surrounds a staple cavity 89100 from the first longitudinal row in its entirety. Stated another way, the first projection 89110 surrounds a proximal end 89102, a distal end 89104, and the intermediate portions of the staple cavity sidewalls 89105, 89107 extending between the proximal end and the distal end of the staple cavity 89100. As shown, the first projection 89110 continuously surrounds a staple cavity 89100 from the first longitudinal row; however, it is also envisioned that numerous discrete projections can cooperate to surround the individual staple cavity 89100 in the first longitudinal row. Projections akin to the first projection 89110 surround all of the staple cavities in the first longitudinal row 89100.

A staple cavity from the second longitudinal row of staple cavities 89200 comprises a corresponding second projection 89210 extending from the deck surface 89010. Each second projection 89210 surrounds a staple cavity 89200 from the second longitudinal row to a second degree. The second degree is less than the first degree surrounded by the first projections 89110 in the first longitudinal row of staple cavities 89100. Stated another way, each second projection 89210 surrounds a second length of a perimeter of a staple cavity 89200 from the second longitudinal row. The second length is less than the first length. As shown, each second projection 89210 surrounds a proximal end 89202 and a distal end 89204 of the staple cavity 89200. Each second projection 89210 further surrounds an intermediate portion extending between the proximal end 89202 and the distal end 89204 on a first lateral side 89205 of the staple cavity 89200; however, as depicted, each second projection 89210 does not surround an intermediate portion extending between the proximal end 89202 and the distal end 89204 on a second lateral side 89207 of the staple cavity 89200. Stated another way, the second projection 89210 forms a C-shaped profile around the staple cavities in the second longitudinal row 89200. The second projection 89210 surrounds the lateral side of the staple cavity 89200 that is positioned closer to the longitudinal slot 89005 than the opposing lateral side. As shown, the second projection 89210 continuously surrounds a staple cavity 89200 from the second longitudinal row; however, it is also envisioned that numerous discrete projections can cooperate to surround the individual staple cavity 89200 in the second longitudinal row. Projections akin to the second projection 89210 surround all staple cavities in the second longitudinal row 89200.

A staple cavity from the third longitudinal row of staple cavities 89300 comprises a corresponding third projection 89310. Each third projection 89310 surrounds a staple cavity 89300 from the third longitudinal row to a third degree. The third degree is less than the first degree surrounded by the first projections 89110 in the first longitudinal row of staple cavities 89100, and the third degree is less than the second degree surrounded by the second projections 89210 in the second longitudinal row of staple cavities 89200. Stated another way, each third projection 89310 surrounds a third length of a perimeter of a staple cavity 89300 from the third longitudinal row. The third length is less than the second length and the first length. As shown, the third projection 89310 surrounds a proximal end 89302 and a distal end 89304 of the staple cavity 89300. Intermediate portions extending between the proximal end 89302 and the distal end 89304 are left unsurrounded. Stated another way, the third projection 89310 surrounds only the proximal and distal ends of staple cavities in the third longitudinal row 89300. Projections akin to the third projection 89310 surround all staple cavities in the third longitudinal row 89300.

As depicted in FIG. 7, the projections 89110, 89210, 89310 from each of the three longitudinal rows of staple cavities 89100, 89200, 89300 are interconnected with one another. Such interconnections serve to improve tissue grip and compression, for example. Such interconnections are extend less than two-thirds the length of one lateral side of a staple cavity; however, the interconnections can extend any suitable length. As discussed above, a first staple cavity 89100a from the first longitudinal row 89100 comprises a proximal end 89102 and a distal end 89104. A first staple cavity 89200a from the second longitudinal row 89200 comprises a proximal end 89202 and a distal end 89204, and a second staple cavity 89200b from the second longitudinal row 89200 comprises a proximal end 89202b and a distal end 89204b. A first staple cavity 89300a from the third longitudinal row 89300 comprises a proximal end 89302 and a distal end 89304.

The first projection 89110 surrounding the first staple cavity 89100a from the first longitudinal row 89100 is continuously coupled to, or otherwise integral with, the second projection 89210 surrounding the first staple cavity 89200a from the second longitudinal row and the second staple cavity 89200b from the second longitudinal row 89200. More specifically, the first projection 89110 is coupled to the second projection 89210 surrounding the first staple cavity 89200a from the second longitudinal row 89200 at a distal end 89204 of the first staple cavity 89100a from the first longitudinal row and a proximal end 89202 of the first staple cavity 89200a from the second longitudinal row 89200. The first projection 89110 is further coupled to the second projection 89210 surrounding the second staple cavity 89200b from the second longitudinal row 89200 at a proximal end 89202 of the first staple cavity 89100a from the first longitudinal row 89100 and a distal end 89204b of the second staple cavity 89200b from the second longitudinal row 89200.

The second projection 89210 surrounding the first staple cavity 89200a from the second longitudinal row 89200 is continuously coupled to, or otherwise integral with, the third projection 89310 surrounding the distal end 89304 of the first staple cavity 89300a from the third longitudinal row 89300. While the third projection 89310 surrounding the proximal end 89304 of the first staple cavity 89300a from the third longitudinal row 89300 is shown discrete from, or otherwise independent of, surrounding projections, it is envisioned the third projection 89310 surrounding the proximal end 89304 could be coupled to the second projection 89210 surrounding the distal end 89204b of the second staple cavity 89200b from the second longitudinal row 89200. Such described interconnections between the projections are repeated along the longitudinal length of the staple cartridge 89000 and mirrored across the longitudinal slot 89005.

As described above, each first projection 89110 at least partially surrounds a first staple cavity 89100 along a first perimeter length of the first staple cavity 89100, each second projection 89210 at least partially surrounds a second staple cavity 89200 along a second perimeter length of the second staple cavity 89200, and each third projection 89310 at least partially surrounds a third staple cavity 89300 along a third perimeter length of the third staple cavity 89300. As also described above, the first perimeter length is longer than the second perimeter length and the second perimeter length is longer than the third perimeter length. Owing to the longer the first perimeter length of the first projections 89100, the first projections 89110 can have a larger contact area with the patient tissue positioned against the deck surface 89010 than the second projections 89200 and the third projections 89300. The larger contact area provided by the first projections 89110 can provide the staple cartridge 89000 with a greater control over the patient tissue around the first staple cavities 89100 as compared to the second staple cavities 89200 and the third staple cavities 89300. As discussed above, the firing driver cuts the patient tissue adjacent the first staple cavities 89100 and providing a high degree of control over the patient tissue over and around the first staple cavities 89100 can reduce, for example, the possibility of the patient tissue bunching up in front of the firing driver and/or the firing driver tearing the patient tissue. Likewise, the second projections 89210 can have a larger contact area with the patient tissue positioned against the deck surface 89010 than the third projections 89310 and, as a result, the staple cartridge 89000 can provide greater control over the patient tissue around the second staple cavities 89200 as compared to the third staple cavities 89300. Moreover, as a result of the above, the patient tissue over and around the third staple cavities 89300 may experience less stress and strain than the patient tissue over and around the second staple cavities 89200 and the first staple cavities 89100. Similarly, as a result of the above, the patient tissue over and around the second staple cavities 89200 may experience less stress and strain the patient tissue over and around the first staple cavities 89100. As a result of the above, the patient tissue can be tightly controlled over and around the first staple cavities 89100, albeit with a high amount of stress and strain within that region of the patient tissue, and more loosely controlled over and around the third staple cavities 89300 resulting in a lower amount of stress and strain within that region of the patient tissue.

Figure 9:
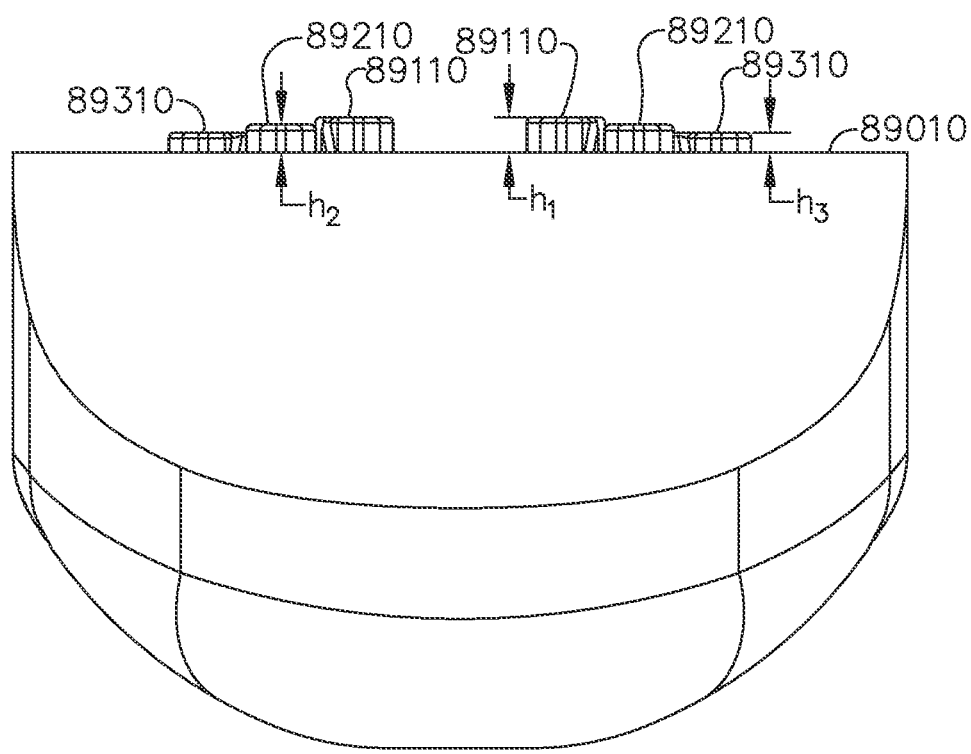
FIG. 9 is a partial elevational view of the staple cartridge of FIG. 7.

In addition to the above, the control over the patient tissue can be improved by varying the height to which each projection extends from the deck surface 89010. As shown in FIG. 9, the first projections 89110 extend from the deck surface 89010 to a first height h1, the second projections 89210 extend from the deck surface 89010 to a second height h2, and the third projections 89310 extend from the deck surface 89010 to a third height h3. The first height h1 is greater than the second height h2 and the third height h3. The second height h2 is greater than the third height h3. The additional support provided to staples in the first longitudinal row 89100 by having taller projections 89110 improves the likelihood of forming a tighter staple along the cut line, as the increased support enables more staple leg forming distance by maintaining the staple in an optimal upright orientation. In the optimal upright orientation, the staples are deployed substantially perpendicular to the deck surface 89010 during the staple firing stroke. When the staples are maintained in the optimal upright orientation, the formation of such staples results in a desired, rounded "B" shape.

As discussed above, the staple cartridge 89000 can be intend to be seated in a channel of an end effector. The staple cartridge 89000 and the channel are configured to oppose an anvil of the end effector, and the end effector is configured to be moved into a fully-closed configuration to clamp target tissue between the anvil and the staple cartridge 89000. When the end effector is in the fully-closed position, a first tissue gap is defined between the first projections 89110 and a cartridge-facing surface of the anvil. A second tissue gap is defined between the second projections 89210 and the cartridge-facing surface of the anvil. A third tissue gap is defined between the third projections 89310 and the cartridge-facing surface of the anvil. Due at least in part to the first height h1 of the first projections 89110 being greater than the second height h2 of the second projections 89210 and the third height h3 of the third projections 89310, the first tissue gap is smaller than the second tissue gap and the third tissue gap. Due at least in part to the second height h2 of the second projections 89210 being greater than the third height h3 of the third projections 89310, the second tissue gap is smaller than the third tissue gap. Providing a smaller tissue gap along the first longitudinal row 89100 results in a greater tissue compression adjacent the longitudinal slot 89005. Such greater tissue compression adjacent the longitudinal slot 89005 serves to maintain the tissue closest to the longitudinal slot 89005 in position during a staple firing stroke, for example. Decreasing the tissue compression laterally away from the longitudinal slot 89005 further allows for the flowable contents of the tissue, such as blood, for example, to flow laterally away from the cut line as the tissue is compressed. Moreover, the presence of projections should be weighed against any potential damage to the adjacent tissue. In addition, the frequency of the projections and/or the geometry of the projections, for example, should also be weighed.

Each projection can extend from the deck surface 89010 to a single, uniform height.

Further to the above, the deck surface 89010 comprises a recessed valley, or a plurality of valleys, amongst the projections 89110, 89210, 89310. As the patient tissue is compressed between the staple cartridge 89000 and the opposing anvil, the patient tissue conforms, flows, and/or or otherwise moves into the recessed valleys. To minimize tissue damage, and/or reduce stress and strain within the patient tissue, for example, it is desirable to increase the surface area of the deck surface 89010, or valleys, between surrounding projections. Increasing this surface area reduces the pressure experienced by the tissue as it conforms around the projections and into the valley areas. A minimum ideal deck surface, or valley, area can be calculated by considering the heights of the projections, the widths of the projections, and/or the pressure induced on the adjacent tissue by the projections. An optimal surface area of the valleys may be double the area of the surrounding projections. An optimal surface area of the valleys may be at least double the area of the surrounding projections. An optimal surface area of the valleys may be triple the area of the surrounding projections.

Referring to FIG. 8, local valleys 89012, 89015, 89017 are defined on the deck surface 89010 by surrounding projections. More specifically, a first staple cavity 89100*a* from a first longitudinal row, a second staple cavity 89100*b* from the first longitudinal row, and a second staple cavity 89200*b* from a second longitudinal row surround a first valley 89012. The first valley 89012 is further bounded by the local deck surface, or a first valley floor. The first valley 89012 comprises a first open end that faces, or otherwise opens, toward the longitudinal slot 89005. The first valley 89012 further comprises a first closed, or bounded end.

The first staple cavity 89100*a* from the first longitudinal row, a first staple cavity 89200*a* from the second longitudinal row, the second staple cavity 89200*b* from the second longitudinal row, and a first staple cavity 89300*a* from a third longitudinal row surround a second valley 89015. The second valley 89015 is S-shaped or Z-shaped, for example, but can comprise any suitable configuration. Moreover, the second valley 89015 is circuitous and comprises at least one laterally-extending region and at least one longitudinally-extending region. An intermixing of laterally-extending regions and longitudinally-extending regions in a valley can provide both lateral and longitudinal control over the flow of patient tissue. The second valley 89015 is further bounded by the local deck surface, or a second valley floor. The second valley 89015 comprises a second open end that opposes, or otherwise opens away from, the longitudinal slot 89005. The second valley 89015 further comprises a second closed, or bounded end. The projections 89110, 89210, 89310 that surround such cavities 89100*a*, 89200*a*, 89200*b*, 89300*a* extend from the deck surface 89010 and define a perimeter of the valley 89015.

The area of the second valley 89015 is greater than the area of the local surrounding projection area. The local surrounding projection area of the valley 89015 includes the area of anvil-facing surfaces of the projections 89110, 89210, 89310 surrounding the staple cavities 89100*a*, 89200*a*, 89200*b*, 89300*a*. While the area of the valley 89015 is ideally larger than the local surrounding projection area, an optimal area of the valley 89015 can be reduced by one-fourth for each ratio of tissue gap to projection height quartile. For example, a tissue gap of 0.100" is defined between the deck surface 89010 and a cartridge-facing surface of an opposing anvil when the end effector is in a fully-closed position. If the heights of the projections are 0.025", the optimal area of the valley 89015 can be reduced by one-fourth, as the heights of the projections extend one-fourth of the tissue gap. If the heights of the projections are 0.050", the optimal area of the valley 89015 can be reduced by one-half, as the heights of the projections extend one-half of the tissue gap.

A third valley 89017 is defined on the deck surface 89010 and is at least partially bounded by a third staple cavity 89100*c* from the first longitudinal row, a third staple cavity 89200*c* from the second longitudinal row, and a third staple cavity 89300*c* from the third longitudinal row. Stated another way, the third valley 89017 is at least partially bounded by the proximal-most staple cavities from the first longitudinal row, the second longitudinal row, and the third longitudinal row. The third valley 89017 is further bounded by the local deck surface, or a third valley floor. The third valley 89017 comprises a third bounded end, and a third open end, wherein the third open end faces, or otherwise opens, toward the proximal end 89002 of the staple cartridge 89000.

The entire disclosures of U.S. Pat. No. 11,589,865, entitled METHODS FOR CONTROLLING A POWERED SURGICAL STAPLER THAT HAS SEPARATE ROTARY CLOSURE AND FIRING SYSTEMS, which issued on Feb. 28, 2023, U.S. Pat. No. 6,978,921, entitled SURGICAL STAPLING INSTRUMENT INCORPORATING AN E-BEAM FIRING MECHANISM, which issued on Dec. 27, 2005, U.S. Pat. No. 10,213,203, entitled STAPLE CARTRIDGE ASSEMBLY WITHOUT A BOTTOM COVER, which issued on Feb. 26, 2019, U.S. Pat. No. 10,945,727, entitled STAPLE CARTRIDGE WITH DEFORMABLE DRIVER RETENTION FEATURES, which issued on Mar. 16, 2021, U.S. Pat. No. 11,234,698, entitled STAPLING SYSTEM COMPRISING A CLAMP LOCKOUT AND A FIRING LOCKOUT, which issued on Feb. 1, 2022, U.S. Pat. No. 11,540,826, entitled SURGICAL STAPLER END EFFECTOR SLED HAVING CARTRIDGE WALL SUPPORT FEATURE, which issued on Jan. 3, 2023, U.S. Pat. No. 10,299,792, entitled FASTENER CARTRIDGE COMPRISING NON-UNIFORM FASTENERS, which issued on May 28, 2019, U.S. Pat. No. 8,540,133, entitled STAPLE CARTRIDGE, which issued on Sep. 24, 2013, U.S. Pat. No. 9,788,835, entitled DEVICES AND METHODS FOR FACILITATING EJECTION OF SURGICAL FASTENERS FROM CARTRIDGES, which issued on Oct. 17, 2017, U.S. Pat. No. 10,105,142, entitled SURGICAL STAPLER WITH PLURALITY OF CUTTING ELEMENTS, which issued on Oct. 23, 2018, U.S. Pat. No. 10,537,324, entitled STEPPED STAPLE CARTRIDGE WITH ASYMMETRICAL STAPLES, which issued on Jan. 21, 2020, U.S. Pat. No. 7,669,746, entitled STAPLE CARTRIDGES FOR FORMING STAPLES HAVING DIFFERING FORMED STAPLE HEIGHTS, which issued on Mar. 2, 2010, U.S. Pat. No. 8,123,100, entitled SURGICAL STAPLING INSTRUMENTS INCLUDING A CARTRIDGE HAVING MULTIPLE STAPLE SIZES, which issued on Feb. 28, 2012, U.S. Pat. No. 7,407,075, entitled STAPLE CARTRIDGE HAVING MULTIPLE STAPLE SIZES FOR A SURGICAL STAPLING INSTRUMENT, which issued on Aug. 5, 2008, U.S. Pat. No. 10,085,749, entitled SURGICAL APPARATUS WITH CONDUCTOR STRAIN RELIEF, which issued on Oct. 2, 2018, U.S. Pat. No. 10,765,427, entitled METHOD FOR ARTICULATING A SURGICAL INSTRUMENT, which issued on Sep. 8, 2020, U.S. Pat. No. 11,291,445, entitled SURGICAL STAPLE CARTRIDGES WITH INTEGRAL AUTHENTICATION KEYS, which issued on Apr. 5, 2022, U.S. Pat. No. 8,864,007, entitled IMPLANTABLE FASTENER CARTRIDGE HAVING A NON-UNIFORM ARRANGEMENT, which issued on Oct. 21, 2014, U.S. Pat. No. 11,490,890, entitled COMPRESSIBLE NON-FIBROUS ADJUNCTS, which issued on Nov. 8, 2022, U.S. Pat. No. 10,952,724, entitled THREE DIMENSIONAL ADJUNCTS, which issued on Mar. 23, 2021, U.S. Pat. No. 9,770,245, entitled LAYER ARRANGEMENTS FOR SURGICAL STAPLE CARTRIDGES, which issued on Sep. 26, 2017, U.S. Pat. No. 10,123,798, entitled TISSUE THICK- NESS COMPENSATOR COMPRISING CONTROLLED RELEASE AND EXPANSION, which issued on Nov. 13, 2018, U.S. Pat. No. 10,166,023, entitled METHOD OF APPLYING A BUTTRESS TO A SURGICAL STAPLER END EFFECTOR, which issued on Jan. 1, 2019, U.S. Pat. No. 11,207,065, entitled METHOD FOR FABRICATING SURGICAL STAPLER ANVILS, which issued on Dec. 28, 2021, U.S. Pat. No. 8,141,762, entitled SURGICAL STAPLER COMPRISING A STAPLE POCKET, which issued on Mar. 27, 2012, U.S. Pat. No. 8,876,857, entitled END EFFECTOR WITH REDUNDANT CLOSING MECHANISMS, which issued on Nov. 4, 2014, U.S. Pat. No. 9,629,631, entitled COMPOSITE DRIVE BEAM FOR SURGICAL STAPLING, which issued on Apr. 25, 2017, U.S. Patent Application Publication No. 2022/0346858, entitled METHOD FOR OPERATING A SURGICAL INSTRUMENT INCLUDING SEGMENTED ELECTRODES, which published on Nov. 3, 2022, U.S. Patent Application Publication No. 2022/0304680, entitled DRIVERS FOR FASTENER CARTRIDGE ASSEMBLIES HAVING ROTARY DRIVE SCREWS, which published on Sep. 29, 2022, U.S. Patent Application Publication No. 2022/0304679, entitled METHOD OF USING A POWERED STAPLING DEVICE, which published on Sep. 29, 2022, U.S. Patent Publication No. 2019/0298350, entitled METHODS FOR CONTROLLING A POWERED SURGICAL STAPLER THAT HAS SEPARATE ROTARY CLOSURE AND FIRING SYSTEMS, which published on Oct. 3, 2019, U.S. Patent Application Publication No. 2017/0367695, entitled STAPLE CARTRIDGE COMPRISING WIRE STAPLES AND STAMPED STAPLES, which published on Dec. 28, 2017, U.S. Patent Application Publication No. 2015/0134077, entitled SEALING MATERIALS FOR USE IN SURGICAL STAPLING, which published on May 14, 2015, U.S. Patent Application Publication No. 2018/0168615, entitled METHOD OF DEFORMING STAPLES FROM TWO DIFFERENT TYPES OF STAPLE CARTRIDGES WITH THE SAME SURGICAL STAPLING INSTRUMENT, which published on Jun. 21, 2018, U.S. Patent Application Publication No. 2018/0132849, entitled STAPLE FORMING POCKET CONFIGURATIONS FOR CIRCULAR SURGICAL STAPLER ANVIL, which published on May 17, 2018, U.S. Patent Application Publication No. 2018/0168613, entitled SURGICAL INSTRUMENTS WITH JAWS THAT ARE PIVOTABLE ABOUT A FIXED AXIS AND INCLUDE SEPARATE AND DISTINCT CLOSURE AND FIRING SYSTEMS, which published on Jun. 21, 2018, U.S. Patent Application Publication No. 2017/0319205, entitled POWERED END EFFECTOR ASSEMBLY WITH PIVOTABLE CHANNEL, which published on Nov. 9, 2017, U.S. Patent Application Publication No. 2014/0001231, entitled FIRING SYSTEM LOCKOUT ARRANGEMENTS FOR SURGICAL INSTRUMENTS, which published on Jan. 2, 2014, U.S. Patent Application Publication No. 2016/0095596, entitled APPARATUS FOR ENDOSCOPIC PROCEDURES, which published on Apr. 7, 2016, U.S. Patent Application Publication No. 2015/0297199, entitled ADAPTER ASSEMBLY WITH GIMBAL FOR INTERCONNECTING ELECTROMECHANICAL SURGICAL DEVICES AND SURGICAL LOADING UNITS, AND SURGICAL SYSTEMS THEREOF, which published on Oct. 22, 2015, U.S. Patent Application Publication No. 2022/0031351, entitled SURGICAL INSTRUMENTS WITH DIFFERENT ARTICULATION JOINT ARRANGEMENTS FOR ACCOMMODATING FLEXIBLE ACTUATORS, which published on Feb. 3, 2022, U.S. Patent Application Publication No. 2022/0031320, entitled SURGICAL INSTRUMENTS WITH FLEXIBLE FIRING MEMBER ACTUATOR CONSTRAINT ARRANGEMENTS, which published on Feb. 3, 2022, U.S. Patent Application Publication No. 2023/0119119, entitled CABLE-DRIVEN ACTUATION SYSTEM FOR ROBOTIC SURGICAL TOOL ATTACHMENT, which published on Apr. 20, 2023, International Patent Publication No. WO2018/071497, entitled STAPLER CARTRIDGE WITH AN INTEGRAL KNIFE, which published on Apr. 18, 2018, International Patent Publication No. WO2018/049211, entitled WRIST ARCHITECTURE, which published on Mar. 15, 2018, U.S. Pat. No. 11,298,129, entitled METHOD FOR PROVIDING AN AUTHENTICATION LOCKOUT IN A SURGICAL STAPLER WITH A REPLACEABLE CARTRIDGE, which issued on Apr. 12, 2022, U.S. Pat. No. 10,898,183, entitled ROBOTIC SURGICAL INSTRUMENT WITH CLOSED LOOP FEEDBACK TECHNIQUES FOR ADVANCEMENT OF CLOSURE MEMBER DURING FIRING, which issued on Jan. 26, 2021, U.S. Pat. No. 5,485,947, entitled LINEAR STAPLING MECHANISM WITH CUTTING MEANS, which issued on Jan. 23, 1996, International Patent Publication No. WO2018/049206, entitled STAPLER RELOAD DETECTION AND IDENTIFICATION, which published on Mar. 15, 2018, U.S. Patent Application Publication No. 2016/0249920, entitled Surgical fastener applying apparatus, which published on Sep. 1, 2016, U.S. Design Pat. No. D974,560, entitled STAPLE CARTRIDGE, which issued on Jan. 3, 2023, U.S. Design Pat. No. D967,421, entitled STAPLE CARTRIDGE, which issued on Oct. 18, 2022, U.S. Design Pat. No. D933,220, entitled BUTTRESS ASSEMBLY FOR A SURGICAL STAPLER, which issued on Oct. 12, 2021, U.S. Pat. No. 9,839,420, entitled TISSUE THICKNESS COMPENSATOR COMPRISING AT LEAST ONE MEDICAMENT, which issued on Dec. 12, 2017, U.S. Pat. No. 10,588,623, entitled ADHESIVE FILM LAMINATE, which issued on Mar. 17, 2020, U.S. Pat. No. 8,499,992, entitled DEVICE AND METHOD FOR CONTROLLING COMPRESSION OF TISSUE, which issued on Aug. 6, 2013, U.S. Patent Application Publication No. 2022/0378427, entitled STAPLING INSTRUMENT COMPRISING JAW MOUNTS, which published on Dec. 1, 2022, U.S. Pat. No. 10,349,939, entitled METHOD OF APPLYING A BUTTRESS TO A SURGICAL STAPLER, which issued on Jul. 16, 2019, U.S. Pat. No. 9,386,988, entitled RETAINER ASSEMBLY INCLUDING A TISSUE THICKNESS COMPENSATOR, which issued on Jul. 12, 2016, U.S. Pat. No. 9,072,535, entitled SURGICAL STAPLING INSTRUMENTS WITH ROTATABLE STAPLE DEPLOYMENT ARRANGEMENTS, which issued on Jul. 7, 2015, and U.S. Pat. No. 9,844,369, entitled, SURGICAL END EFFECTORS WITH FIRING ELEMENT MONITORING ARRANGEMENTS, which issued on Dec. 19, 2017 are incorporated by reference herein.

The entire disclosures of:
U.S. Pat. No. 5,403,312, entitled ELECTROSURGICAL HEMOSTATIC DEVICE, which issued on Apr. 4, 1995;
U.S. Pat. No. 7,000,818, entitled SURGICAL STAPLING INSTRUMENT HAVING SEPARATE DISTINCT CLOSING AND FIRING SYSTEMS, which issued on Feb. 21, 2006;
U.S. Pat. No. 7,422,139, entitled MOTOR-DRIVEN SURGICAL CUTTING AND FASTENING INSTRUMENT WITH TACTILE POSITION FEEDBACK, which issued on Sep. 9, 2008;

U.S. Pat. No. 7,464,849, entitled ELECTRO-MECHANICAL SURGICAL INSTRUMENT WITH CLOSURE SYSTEM AND ANVIL ALIGNMENT COMPONENTS, which issued on Dec. 16, 2008;

U.S. Pat. No. 7,670,334, entitled SURGICAL INSTRUMENT HAVING AN ARTICULATING END EFFECTOR, which issued on Mar. 2, 2010;

U.S. Pat. No. 7,753,245, entitled SURGICAL STAPLING INSTRUMENTS, which issued on Jul. 13, 2010;

U.S. Pat. No. 8,393,514, entitled SELECTIVELY ORIENTABLE IMPLANTABLE FASTENER CARTRIDGE, which issued on Mar. 12, 2013;

U.S. patent application Ser. No. 11/343,803, entitled SURGICAL INSTRUMENT HAVING RECORDING CAPABILITIES, now U.S. Pat. No. 7,845,537;

U.S. patent application Ser. No. 12/031,573, entitled SURGICAL CUTTING AND FASTENING INSTRUMENT HAVING RF ELECTRODES, filed Feb. 14, 2008;

U.S. patent application Ser. No. 12/031,873, entitled END EFFECTORS FOR A SURGICAL CUTTING AND STAPLING INSTRUMENT, filed Feb. 15, 2008, now U.S. Pat. No. 7,980,443;

U.S. patent application Ser. No. 12/235,782, entitled MOTOR-DRIVEN SURGICAL CUTTING INSTRUMENT, now U.S. Pat. No. 8,210,411;

U.S. patent application Ser. No. 12/235,972, entitled MOTORIZED SURGICAL INSTRUMENT, now U.S. Pat. No. 9,050,083.

U.S. patent application Ser. No. 12/249,117, entitled POWERED SURGICAL CUTTING AND STAPLING APPARATUS WITH MANUALLY RETRACTABLE FIRING SYSTEM, now U.S. Pat. No. 8,608,045;

U.S. patent application Ser. No. 12/647,100, entitled MOTOR-DRIVEN SURGICAL CUTTING INSTRUMENT WITH ELECTRIC ACTUATOR DIRECTIONAL CONTROL ASSEMBLY, filed Dec. 24, 2009, now U.S. Pat. No. 8,220,688;

U.S. patent application Ser. No. 12/893,461, entitled STAPLE CARTRIDGE, filed Sep. 29, 2012, now U.S. Pat. No. 8,733,613;

U.S. patent application Ser. No. 13/036,647, entitled SURGICAL STAPLING INSTRUMENT, filed Feb. 28, 2011, now U.S. Pat. No. 8,561,870;

U.S. patent application Ser. No. 13/118,241, entitled SURGICAL STAPLING INSTRUMENTS WITH ROTATABLE STAPLE DEPLOYMENT ARRANGEMENTS, now U.S. Pat. No. 9,072,535;

U.S. patent application Ser. No. 13/524,049, entitled ARTICULATABLE SURGICAL INSTRUMENT COMPRISING A FIRING DRIVE, filed on Jun. 15, 2012, now U.S. Pat. No. 9,101,358;

U.S. patent application Ser. No. 13/800,025, entitled STAPLE CARTRIDGE TISSUE THICKNESS SENSOR SYSTEM, filed on Mar. 13, 2013, now U.S. Pat. No. 9,345,481;

U.S. patent application Ser. No. 13/800,067, entitled STAPLE CARTRIDGE TISSUE THICKNESS SENSOR SYSTEM, filed on Mar. 13, 2013, now U.S. Patent Application Publication No. 2014/0263552;

U.S. Patent Application Publication No. 2007/0175955, entitled SURGICAL CUTTING AND FASTENING INSTRUMENT WITH CLOSURE TRIGGER LOCKING MECHANISM, filed Jan. 31, 2006; and U.S. Patent Application Publication No. 2010/0264194, entitled SURGICAL STAPLING INSTRUMENT WITH AN ARTICULATABLE END EFFECTOR, filed Apr. 22, 2010, now U.S. Pat. No. 8,308,040, are hereby incorporated by reference herein.

Various aspects of the subject matter described herein are set out in the following examples.

1. A staple cartridge for use with a surgical stapling instrument, wherein said staple cartridge comprises a cartridge body comprising a longitudinal slot extending from a proximal end toward a distal end and a deck defining a local deck area comprising a first staple cavity adjacent said longitudinal slot comprising a pair of first staple cavity ends and a pair of first staple cavity sides and a second staple cavity laterally offset and longitudinally offset relative to said first staple cavity, wherein said second staple cavity comprises a pair of second staple cavity ends and a pair of second staple cavity sides. The cartridge body further comprises a third staple cavity laterally offset and longitudinally offset relative to said second staple cavity, wherein said third staple cavity is laterally offset and longitudinally aligned relative to said first staple cavity, and wherein said third staple cavity comprises a pair of third staple cavity ends and a pair of third staple cavity sides, a first projection extending from said deck, wherein said first projection surrounds a portion of said first staple cavity, a second projection extending from said deck, wherein said second projection surrounds a portion of said second staple cavity, and wherein said first projection and said second projection are connected to one another above said deck, and a pair of third projections extending from said deck, wherein one said third projection surrounds a first portion of said third staple cavity, wherein another said third projection surrounds a second portion of said third staple cavity, wherein said second projection and one said third projection are connected to one another above said deck, wherein said first projection, said second projection, and said pair of third projections define a localized tissue-facing surface area above said deck, wherein a localized valley is defined on said deck between said first projection, said second projection, and said pair of third projections, wherein said localized valley comprises a localized valley area, and wherein said localized valley area is greater than said localized tissue-facing area.

2. The staple cartridge of Example 1, wherein said localized valley area and said localized tissue-facing area combine to form said local deck area.

3. The staple cartridge of Example 2, wherein said localized valley area comprises a largest portion of said local deck area.

4. The staple cartridge of Example 1, wherein a ratio of said localized valley area to said localized tissue-facing area is no less than 1:1 and no greater than 1:7.

5. The staple cartridge of Example 1, wherein said first projection extends from said deck to a first height, wherein said second projection extends from said deck to a second height, and wherein said first height is different than said second height.

6. The staple cartridge of Example 5, wherein said first height is greater than said second height.

7. The staple cartridge of Example 5, wherein said third projection extends from said deck to a third height (h3), wherein said third height is different than said second height and said first height.

8. The staple cartridge of Example 7, wherein said first height is greater than said third height, and wherein said second height is greater than said third height.

9. The staple cartridge of Example 1, wherein said second projection and said first projection are coupled to one another along less than two-thirds of a length of said other first cavity side.
10. The staple cartridge of Example 1, further comprising: a first flexible tab positioned in said first staple cavity, wherein said first flexible tab is configured to support a first staple in a desired first position therein; and a second flexible tab positioned in said second staple cavity, wherein said second flexible tab is configured to support a second staple in a desired second position therein.
11. The staple cartridge of Example 10, wherein said first flexible tab is configured to temporarily non-movably support said first staple therein, wherein said second flexible tab is configured to temporarily non-movably support said second staple therein, and wherein said third flexible tab is configured to temporarily non-movably support said third staple therein.
12. The staple cartridge of Example 10, wherein said first staple is selected from a group of first staples, wherein said first staples are formed from first staple wires comprising different first wire diameters, wherein said second staple is selected from a group of second staples, and wherein said second staples are formed from second staple wires comprising different second wire diameters.
13. The staple cartridge of Example 10, wherein said first tab is configured to center said first staple within said first staple cavity, and wherein said second tab is configured to center said second staple within said second staple cavity.
14. The staple cartridge of Example 10, wherein said first tab is configured to center said first staple within said first staple cavity, wherein said first tab is configured to center a third staple within said first staple cavity in lieu of said first staple, wherein said first staple comprises a first diameter, wherein said third staple comprises a third diameter, and wherein said first diameter is different than said third diameter.
15. The staple cartridge of Example 1, wherein said local deck area further comprises another second staple cavity longitudinally aligned with said second staple cavity, wherein said another second staple cavity comprises a pair of another second staple cavity ends and a pair of another second staple cavity sides, wherein said localized valley is defined between said first staple cavity, said second staple cavity, said another second staple cavity, and said third staple cavity.
16. A staple cartridge for use with a surgical stapling instrument, wherein said staple cartridge comprises a cartridge body comprising a proximal end, a distal end, a deck, a longitudinal slot extending from said proximal end toward said distal end, a longitudinal row of first staple cavities adjacent said longitudinal slot, a longitudinal row of second staple cavities, and a longitudinal row of third staple cavities, wherein said longitudinal row of second staple cavities is intermediate said longitudinal row of first staple cavities and said longitudinal row of third staple cavities. The cartridge body further comprises a plurality of first projections extending from said deck, wherein each said first projection surrounds a portion of a said first staple cavity, a plurality of second projections extending from said deck, wherein each said second projection surrounds a portion of a said second staple cavity, and wherein each said first projection is connected to a said second projection above said deck, a plurality of third projections extending from said deck, wherein each said third projection surrounds a portion of a said third staple cavity, wherein each said third projection is connected to a said second projection above said deck, a plurality of first valleys, wherein each said first valley is at least partially bounded by a said first projection, a said second projection, and a first valley floor, wherein each said first valley comprises a first open end and a first bounded end, and wherein said first open end faces toward said longitudinal slot, and a plurality of second valleys, wherein each said second valley is at least partially bounded by a said first projection, a said second projection, a said third projection, and a second valley floor, wherein each said second valley comprises a second open end and a second bounded end, and wherein said second open end faces away from said longitudinal slot.
17. The staple cartridge of Example 16, wherein said first valley floor and said second valley floor are defined on said deck.
18. The staple cartridge of Example 16, wherein each said first valley is partitioned from the other said first valleys, and wherein each said second valley is partitioned from the other said second valleys.
19. The staple cartridge of Example 16, wherein each said first valley is partitioned from each said second valley.
20. The staple cartridge of Example 16, further comprising staples removably stored in said first staple cavities, said second staple cavities, and said third staple cavities.
21. A staple cartridge for use with a surgical stapling instrument, wherein said staple cartridge comprises a cartridge body comprising a proximal end, a distal end, a deck, a longitudinal slot extending from said proximal end toward said distal end, a longitudinal row of first staple cavities adjacent said longitudinal slot, wherein each said first staple cavity comprises a first staple cavity perimeter defined in said deck, a longitudinal row of second staple cavities, wherein each said second staple cavity comprises a second staple cavity perimeter defined in said deck, and a longitudinal row of third staple cavities, wherein each said third staple cavity comprises a third staple cavity perimeter defined in said deck, and wherein said longitudinal row of second staple cavities is intermediate said longitudinal row of first staple cavities and said longitudinal row of third staple cavities. The cartridge body further comprises a first projection extending from said deck, wherein said first projection surrounds a first length of a said first staple cavity perimeter, a second projection extending from said deck, wherein said second projection surrounds a second length of a said second staple cavity perimeter, and wherein said first projection is connected to said second projection above said deck, and a third projection extending from said deck, wherein said third projection surrounds a third length of a said third staple cavity perimeter, wherein said third projection is connected to said second projection above said deck, wherein said first length is longer than said second length, and wherein said second length is longer than said third length.
22. The staple cartridge of Example 21, wherein said first projection is taller than said second projection, and wherein said second projection is taller than said third projection.

23. The staple cartridge of Example 21, further comprising staples removably stored in said first staple cavities, said second staple cavities, and said third staple cavities.

24. A staple cartridge comprising a cartridge body comprising a proximal end, a distal end, a deck, a longitudinal slot extending from said proximal end toward said distal end, a staple cavity, a first arm, and a second arm, wherein said first arm and said second arm define a staple gap therebetween defined by a staple gap width, wherein said staple cavity is configured to store a first wire staple and, in lieu of the first staple, a second wire staple, wherein the first wire staple is defined by a first wire diameter and the second staple is defined by a second wire diameter that is different than the first wire diameter, and wherein said staple gap width is smaller than the first wire diameter and the second wire diameter such that said first arm and said second arm are engaged with and co-operatively position the first staple in said staple cavity when the first staple is positioned in said staple cavity and such that said first arm and said second arm are engaged with and co-operatively position the second staple in said staple cavity when the second staple is positioned in said staple cavity.

25. A staple cartridge (88000, 89000) for use with a surgical stapling instrument, wherein said staple cartridge comprises a cartridge body, comprising a longitudinal slot (89005) extending from a proximal end (89002) toward a distal end (89004), a deck (89010) defining a local deck area comprising a first staple cavity (89100a) adjacent said longitudinal slot comprising a pair of first staple cavity ends (89102, 89104) and a pair of first staple cavity sides (89105, 89107), a second staple cavity (89200a) laterally offset and longitudinally offset relative to said first staple cavity, wherein said second staple cavity comprises a pair of second staple cavity ends (89202, 89204) and a pair of second staple cavity sides (89205, 89207), a third staple cavity (89300a) laterally offset and longitudinally offset relative to said second staple cavity, wherein said third staple cavity is laterally offset and longitudinally aligned relative to said first staple cavity, and wherein said third staple cavity comprises a pair of third staple cavity ends (89302, 89304) and a pair of third staple cavity sides (89305, 89307), a first projection (89110) extending from said deck, wherein said first projection surrounds a portion of said first staple cavity, a second projection (89210) extending from said deck, wherein said second projection surrounds a portion of said second staple cavity, and wherein said first projection and said second projection are connected to one another above said deck, and a pair of third projections (89310) extending from said deck, wherein one said third projection surrounds a first portion of said third staple cavity, wherein another said third projection surrounds a second portion of said third staple cavity, wherein said second projection and one said third projection are connected to one another above said deck, wherein first projection, said second projection, and said pair of third projections define a localized tissue-facing surface area above said deck, wherein a localized valley (89015) is defined on said deck between said first projection, said second projection, and said pair of third projections, wherein said localized valley comprises a localized valley area, and wherein said localized valley area is greater than said localized tissue-facing area.

26. The staple cartridge of Example 25, wherein said localized valley area and said localized tissue-facing area combine to form said local deck area.

27. The staple cartridge of Example 26, wherein said localized valley area comprises a largest portion of said local deck area.

28. The staple cartridge of any one of Examples 25 or 26, wherein a ratio of said localized valley area to said localized tissue-facing area is no less than 1:1 and no greater than 1:7.

29. The staple cartridge of any one of Examples 25, 26, 27, or 28, wherein said first projection extends from said deck to a first height (h1), wherein said second projection extends from said deck to a second height (h2), and wherein said first height is different than said second height.

30. The staple cartridge of Example 29, wherein said first height is greater than said second height.

31. The staple cartridge of Example 29, wherein said third projection extends from said deck to a third height (h3), wherein said third height is different than said second height and said first height.

32. The staple cartridge of Example 31, wherein said first height is greater than said third height, and wherein said second height is greater than said third height.

33. The staple cartridge of any one of Examples 25, 26, 27, 28, 29, 30, 31, or 32, wherein said second projection and said first projection are coupled to one another along less than two-thirds of a length of said other first cavity side.

34. The staple cartridge of any one of Examples 25, 26, 27, 28, 29, 30, 31, 32, or 33, further comprising: a first flexible tab (88502a, 88502b, 88504a, 88504b) positioned in said first staple cavity, wherein said first flexible tab is configured to support a first staple in a desired first position therein; and a second flexible tab (88502a, 88502b, 88504a, 88504b) positioned in said second staple cavity, wherein said second flexible tab is configured to support a second staple in a desired second position therein.

35. The staple cartridge of Example 34, wherein said first flexible tab is configured to temporarily non-movably support said first staple therein, wherein said second flexible tab is configured to temporarily non-movably support said second staple therein, and wherein said third flexible tab is configured to temporarily non-movably support said third staple therein.

36. The staple cartridge of any one of Examples 34 or 35, wherein said first staple is selected from a group of first staples, wherein said first staples are formed from first staple wires comprising different first wire diameters, wherein said second staple is selected from a group of second staples, and wherein said second staples are formed from second staple wires comprising different second wire diameters.

37. The staple cartridge of any one of Examples 34, 35, or 36, wherein said first tab is configured to center said first staple within said first staple cavity, and wherein said second tab is configured to center said second staple within said second staple cavity.

38. The staple cartridge of any one of Examples 34, 35, or 36, wherein said first tab is configured to center said first staple within said first staple cavity, wherein said first tab is configured to center a third staple within said first staple cavity in lieu of said first staple, wherein said first staple comprises a first diameter, wherein said third staple comprises a third diameter, and wherein said first diameter is different than said third diameter.

39. The staple cartridge of any one of Examples 25, 26, 27, 28, 29, 30, 31, 32, 33, 34, 35, 36, 37, or 38, wherein said local deck area further comprises another second staple cavity (89200*b*) longitudinally aligned with said second staple cavity, wherein said another second staple cavity comprises a pair of another second staple cavity ends (89202*b*, 89204*b*) and a pair of another second staple cavity sides (89205, 89207), wherein said localized valley is defined between said first staple cavity, said second staple cavity, said another second staple cavity, and said third staple cavity.

In addition to or in lieu of holding the tissue in place during the staple firing stroke, the projections extending from the cartridge deck can grip and/or secure an implantable adjunct, such as a layer of buttress material, for example, against the cartridge deck. Moreover, the projections, especially the projections that at least partially surround the staple cavities, can secure the adjunct in position as staples are ejected from the cavities and/or as the adjunct is severed during a staple firing stroke. Moreover, the projections that are adjacent the staple cavities can be configured to guide and orient the staples as the staples are fired, or ejected, from the cartridge body during the staple firing stroke.

Although various devices have been described herein in connection with certain embodiments, modifications and variations to those embodiments may be implemented. Particular features, structures, or characteristics may be combined in any suitable manner in one or more embodiments. Thus, the particular features, structures, or characteristics illustrated or described in connection with one embodiment may be combined in whole or in part, with the features, structures or characteristics of one or more other embodiments without limitation. Also, where materials are disclosed for certain components, other materials may be used. Furthermore, according to various embodiments, a single component may be replaced by multiple components, and multiple components may be replaced by a single component, to perform a given function or functions. The foregoing description and following claims are intended to cover all such modification and variations.

The devices disclosed herein can be designed to be disposed of after a single use, or they can be designed to be used multiple times. In either case, however, a device can be reconditioned for reuse after at least one use. Reconditioning can include any combination of the steps including, but not limited to, the disassembly of the device, followed by cleaning or replacement of particular pieces of the device, and subsequent reassembly of the device. In particular, a reconditioning facility and/or surgical team can disassemble a device and, after cleaning and/or replacing particular parts of the device, the device can be reassembled for subsequent use. Those skilled in the art will appreciate that reconditioning of a device can utilize a variety of techniques for disassembly, cleaning/replacement, and reassembly. Use of such techniques, and the resulting reconditioned device, are all within the scope of the present application.

The devices disclosed herein may be processed before surgery. First, a new or used instrument may be obtained and, when necessary, cleaned. The instrument may then be sterilized. In one sterilization technique, the instrument is placed in a closed and sealed container, such as a plastic or TYVEK bag. The container and instrument may then be placed in a field of radiation that can penetrate the container, such as gamma radiation, x-rays, and/or high-energy electrons. The radiation may kill bacteria on the instrument and in the container. The sterilized instrument may then be stored in the sterile container. The sealed container may keep the instrument sterile until it is opened in a medical facility. A device may also be sterilized using any other technique known in the art, including but not limited to beta radiation, gamma radiation, ethylene oxide, plasma peroxide, and/or steam.

While this invention has been described as having exemplary designs, the present invention may be further modified within the spirit and scope of the disclosure. This application is therefore intended to cover any variations, uses, or adaptations of the invention using its general principles.

It is worthy to note that any reference numbers included in the appended claims are used to reference exemplary embodiments/elements described in the present disclosure. Accordingly, any such reference numbers are not meant to limit the scope of the subject matter recited in the appended claims.

What is claimed is:

1. A staple cartridge for use with a surgical stapling instrument, wherein said staple cartridge comprises a cartridge body, comprising:
    a longitudinal slot extending from a proximal end toward a distal end;
    a deck defining a local deck area comprising:
        a first staple cavity adjacent said longitudinal slot comprising a pair of first staple cavity ends and a pair of first staple cavity sides;
        a second staple cavity laterally offset and longitudinally offset relative to said first staple cavity, wherein said second staple cavity comprises a pair of second staple cavity ends and a pair of second staple cavity sides;
        a third staple cavity laterally offset and longitudinally offset relative to said second staple cavity, wherein said third staple cavity is laterally offset and longitudinally aligned relative to said first staple cavity, and wherein said third staple cavity comprises a pair of third staple cavity ends and a pair of third staple cavity sides;
        a first projection extending from said deck, wherein said first projection surrounds a portion of said first staple cavity;
        a second projection extending from said deck, wherein said second projection surrounds a portion of said second staple cavity, and wherein said first projection and said second projection are connected to one another above said deck;
        a pair of third projections extending from said deck, wherein one said third projection surrounds a first portion of said third staple cavity, wherein another said third projection surrounds a second portion of said third staple cavity, wherein said second projection and one said third projection are connected to one another above said deck, wherein said first projection, said second projection, and said pair of third projections define a localized tissue-facing surface area above said deck, wherein a localized valley is defined on said deck between said first projection, said second projection, and said pair of third projections, wherein said localized valley comprises a localized valley area, and wherein said localized valley area is greater than said localized tissue-facing area.

2. The staple cartridge of claim 1, wherein said localized valley area and said localized tissue-facing area combine to form said local deck area.

3. The staple cartridge of claim 2, wherein said localized valley area comprises a largest portion of said local deck area.

4. The staple cartridge of claim 1, wherein a ratio of said localized valley area to said localized tissue-facing area is no less than 1:1 and no greater than 1:7.

5. The staple cartridge of claim 1, wherein said first projection extends from said deck to a first height, wherein said second projection extends from said deck to a second height, and wherein said first height is different than said second height.

6. The staple cartridge of claim 5, wherein said first height is greater than said second height.

7. The staple cartridge of claim 5, wherein each third projection of said pair of third projections extends from said deck to a third height, wherein said third height is different than said second height and said first height.

8. The staple cartridge of claim 7, wherein said first height is greater than said third height, and wherein said second height is greater than said third height.

9. The staple cartridge of claim 1, wherein said second projection and said first projection are coupled to one another along less than two-thirds of a length of said pair of first staple cavity sides.

10. The staple cartridge of claim 1, further comprising:
a first flexible tab positioned in said first staple cavity, wherein said first flexible tab is configured to support a first staple in a desired first position therein; and
a second flexible tab positioned in said second staple cavity, wherein said second flexible tab is configured to support a second staple in a desired second position therein.

11. The staple cartridge of claim 10, wherein said first flexible tab is configured to temporarily non-movably support said first staple therein, wherein said second flexible tab is configured to temporarily non-movably support said second staple therein, and wherein a third flexible tab is configured to temporarily non-movably support a third staple in a desired third position therein.

12. The staple cartridge of claim 10, wherein said first staple is selected from a group of first staples, wherein said first staples are formed from first staple wires comprising different first wire diameters, wherein said second staple is selected from a group of second staples, and wherein said second staples are formed from second staple wires comprising different second wire diameters.

13. The staple cartridge of claim 10, wherein said first tab is configured to center said first staple within said first staple cavity, and wherein said second tab is configured to center said second staple within said second staple cavity.

14. The staple cartridge of claim 10, wherein said first tab is configured to center said first staple within said first staple cavity, wherein said first tab is configured to center a third staple within said first staple cavity in lieu of said first staple, wherein said first staple comprises a first diameter, wherein said third staple comprises a third diameter, and wherein said first diameter is different than said third diameter.

15. The staple cartridge of claim 1, wherein said local deck area further comprises another second staple cavity longitudinally aligned with said second staple cavity, wherein said another second staple cavity comprises a pair of another second staple cavity ends and a pair of another second staple cavity sides, wherein said localized valley is defined between said first staple cavity, said second staple cavity, said another second staple cavity, and said third staple cavity.

16. A staple cartridge for use with a surgical stapling instrument, wherein said staple cartridge comprises a cartridge body, comprising:
a proximal end;
a distal end;
a deck;
a longitudinal slot extending from said proximal end toward said distal end;
a longitudinal row of first staple cavities adjacent said longitudinal slot;
a longitudinal row of second staple cavities;
a longitudinal row of third staple cavities, wherein said longitudinal row of second staple cavities is intermediate said longitudinal row of first staple cavities and said longitudinal row of third staple cavities;
a plurality of first projections extending from said deck, wherein each said first projection surrounds a portion of a said first staple cavity;
a plurality of second projections extending from said deck, wherein each said second projection surrounds a portion of a said second staple cavity, and wherein each said first projection is connected to a said second projection above said deck;
a plurality of third projections extending from said deck, wherein each said third projection surrounds a portion of a said third staple cavity, wherein each said third projection is connected to a said second projection above said deck;
a plurality of first valleys, wherein each said first valley is at least partially bounded by a said first projection, a said second projection, and a first valley floor, wherein each said first valley comprises a first open end and a first bounded end, and wherein said first open end faces toward said longitudinal slot; and
a plurality of second valleys, wherein each said second valley is at least partially bounded by a said first projection, a said second projection, a said third projection, and a second valley floor, wherein each said second valley comprises a second open end and a second bounded end, and wherein said second open end faces away from said longitudinal slot.

17. The staple cartridge of claim 16, wherein said first valley floor and said second valley floor are defined on said deck.

18. The staple cartridge of claim 16, wherein each said first valley is partitioned from the other said first valleys, and wherein each said second valley is partitioned from the other said second valleys.

19. The staple cartridge of claim 16, wherein each said first valley is partitioned from each said second valley.

20. The staple cartridge of claim 16, further comprising staples removably stored in said first staple cavities, said second staple cavities, and said third staple cavities.

* * * * *